US00RE48923E

(19) United States
(12) Reissued Patent
Califano et al.

(10) Patent Number: US RE48,923 E
(45) Date of Reissued Patent: Feb. 8, 2022

(54) CRYSTAL FORMS

(71) Applicant: AbbVie Inc., North Chicago, IL (US)

(72) Inventors: Jean-Christophe Califano, Whitefish Bay, WI (US); Michael G. Fickes, Lake Bluff, IL (US); Lars Fredrik Nordstroem, Evanston, IL (US)

(73) Assignee: AbbVie Inc., North Chicago, IL (US)

(21) Appl. No.: 15/830,544

(22) Filed: Dec. 4, 2017

Related U.S. Patent Documents

Reissue of:
(64) Patent No.: 9,593,078
Issued: Mar. 14, 2017
Appl. No.: 14/707,433
Filed: May 8, 2015

U.S. Applications:
(60) Provisional application No. 61/991,242, filed on May 9, 2014.

(51) Int. Cl.

| | |
|---|---|
| ***C07D 401/14*** | (2006.01) |
| ***C07D 207/16*** | (2006.01) |
| ***C07D 405/14*** | (2006.01) |
| ***C07D 413/14*** | (2006.01) |
| ***A61K 38/05*** | (2006.01) |
| ***A61K 31/4178*** | (2006.01) |
| ***C07D 401/10*** | (2006.01) |
| ***C07D 403/14*** | (2006.01) |
| ***C07D 417/14*** | (2006.01) |
| ***C07D 519/00*** | (2006.01) |

(52) U.S. Cl.
CPC ..... *C07D 207/16* (2013.01); *A61K 31/4178* (2013.01); *A61K 38/05* (2013.01); *C07D 401/10* (2013.01); *C07D 401/14* (2013.01); *C07D 403/14* (2013.01); *C07D 405/14* (2013.01); *C07D 413/14* (2013.01); *C07D 417/14* (2013.01); *C07D 519/00* (2013.01)

(58) Field of Classification Search
CPC .. C07D 207/16; C07D 401/14; C07D 519/00; C07D 417/14; C07D 403/14; C07D 401/10; C07D 405/14; C07D 413/14; A61K 31/4178; A61K 38/05
See application file for complete search history.

(56) References Cited

U.S. PATENT DOCUMENTS 8,937,150 B2 * 1/2015 DeGoey ..... A61K 31/4439 530/206
2012/0004196 A1 1/2012 Degoey et al.

FOREIGN PATENT DOCUMENTS

EP 2283822 A2 * 2/2011 ..... A61P 43/00
JP 2013539791 A 10/2013
JP 2017515897 A 6/2017
WO WO-2012051361 A1 * 4/2012 ..... A61K 31/4418
WO WO-2013025449 A1 * 2/2013 ..... A61K 31/444

OTHER PUBLICATIONS

Braga D., et al., "Crystal Polymorphism and Multiple Crystal Forms," Structure and Bonding, Feb. 2009, vol. 132, pp. 25-50.
Caira M.R., "Crystalline Polymorphism of Organic Compounds," Topics in Current Chemistry,1998, vol. 198, pp. 163-208.
Hilfiker R., et al., "Relevance of Solid-state Properties for Pharmaceutical Products," Polymorphism: in the Pharmaceutical Industry, 2006, pp. 1-19.
Office Action dated Mar. 19, 2019 for Mexican Patent Application No. MX/a/2016/014459, 8 pages (with English translation).
Masakuni Matsuoka, "Kesshoutakei no kiso to ouyou" (Fundamentals and applications of crystalline polymorphism), CMC Publishing Co., Ltd., Oct. 22, 2010, a popular edition, first copy, pp. 105-117, pp. 181-191.
Brandrup J., et al., Polymer Handbook, 2nd Edition, John Wiley & Sons, 1975, Table of Contents.
Fiedler., "Encyclopedia of Excipients for Pharmaceuticals, Cosmetics and related Areas," 5th Edition, Hoepfner E. M., et al., eds., Editio Cantor Verlag Aulendorf, 2002, Table of Contents.
Masters K., "Spray Drying Handbook" 4th Edition, John Wiley & Sons, 1985, Table of Contents.
Sperling L. H., "Introduction to Physical Polymer Science," 2nd Edition, John Wiley & Sons, Inc., 1992, Table of Contents, 18 pages.
International Search Report for PCT/US2015/029842, 3 pages. Sep. 16, 2015.

* cited by examiner

*Primary Examiner* — Dwayne C. Jones

(57) ABSTRACT

The present invention features crystalline forms of Compound I. In one embodiment, a crystalline form of Compound I has characteristic peaks in the PXRD pattern as shown in one of FIGS. 1-10.

22 Claims, 10 Drawing Sheets

CRYSTAL FORMS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATION

This application *is a reissue application of U.S. Pat. No. 9,593,078, which issued on Mar. 14, 2017 from U.S. Utility application Ser. No. 14/707,433, which was filed on May 8, 2015 and* claims the benefit of U.S. Provisional Application Ser. No. 61/991,242, filed May 9, 2014, the contents of which are incorporated herein by reference.

FIELD OF THE INVENTION

The present invention relates to crystalline polymorphs of Compound I, pharmaceutical compositions comprising the same, and methods of using the same to prepare pharmaceutical compositions.

BACKGROUND

The hepatitis C virus (HCV) is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often inadequate. Therefore, there is a need for new drugs to treat HCV infection.

BRIEF DESCRIPTION OF THE DRAWINGS

The drawings are provided for illustration, not limitation.

DETAILED DESCRIPTION

The present invention features crystalline polymorphs of methyl {(2S,3R)-1- [(2S)-2 -{5-[(2R,5R)-1-{3,5-difluoro-4 [4-(4-fluorophenyl)piperidin-1-yl]phenyl}-5-(6-fluoro-2{(2S)-1-[N-(methoxycarbonyl)-O-methyl-L-threonyl]pyrrolidin-2-yl}-1H-benzimidazol-5-yl)pyrrolidin-2-yl]-6-fluoro-1H-benzimidazol-2-yl}pyrrolidin-1-yl]-3-methoxy-1-oxobutan-2-yl}carbamate

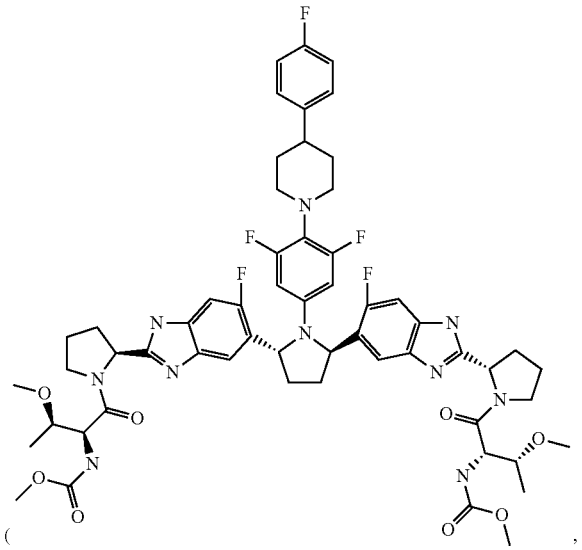

herein "Compound I"). Compound I is a potent HCV NS5A inhibitor and is described in U.S. Patent Application Publication No. 2012/0004196, which is incorporated herein by reference in its entirety.

Compound I was found to be very difficult to crystallize during early development. Crystalline Compound I was not readily obtained despite months of development work. Even if a crystalline form of Compound I had been known to exit, the precise crystal structure of the crystalline form would generally not have been predictable.

A crystalline form of Compound I was unexpectedly obtained using a highly unconventional solvent system—namely, n-butylamine. Additional crystalline forms were subsequently identified. Prior to the isolation and characterization of these crystalline forms, the existence and identity of these particular polymorphs had not been expected. These crystalline forms can be used to improve formulation (e.g., via hot melt extrusion), allow for purification via crystallization as well as manufacturing at scale, and enable improved stability, handling and bulk properties among others.

Figure 1:
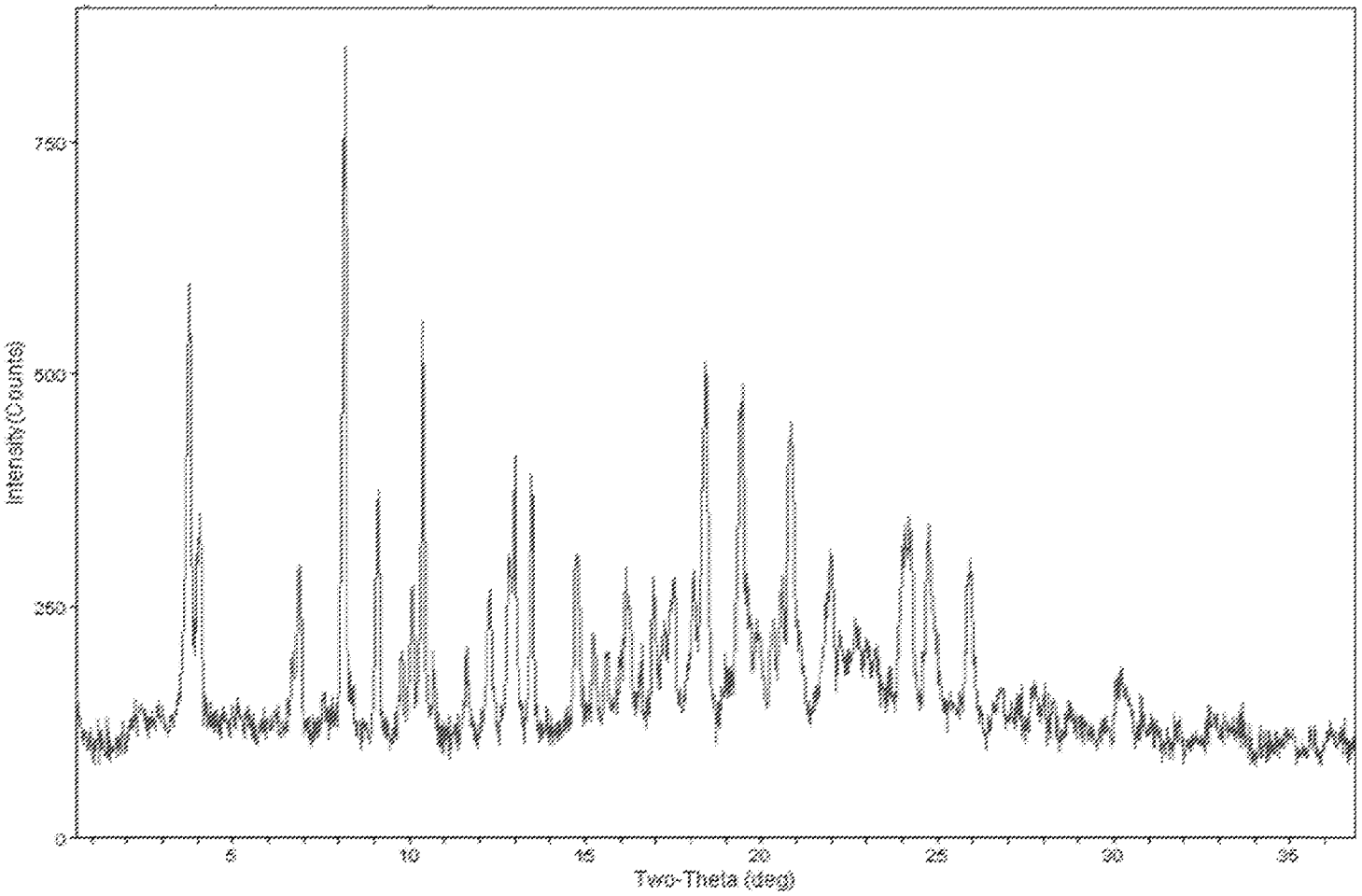
FIG. 1 shows experimental PXRD patterns of Compound I n-butylamine-H2O solvate (Pattern A or Form I).

In one aspect, the invention features a crystalline form of Compound I which has characteristic peaks in the powder X-ray diffraction (PXRD) pattern as shown in FIG. 1.

In another aspect, the invention features a crystalline form of Compound I which has characteristic peaks in the powder X-ray diffraction (PXRD) pattern at values of two theta (° 2θ) as shown in Table 1.

The relative intensity, as well as the two theta value, of each peak in Tables 1-10 and FIGS. 1-10 may change or shift under certain conditions, although the crystalline form is the same. One of ordinary skill in the art should be able to readily determine whether a given crystalline form is the same crystalline form as described in one of FIGS. 1-10 or Tables 1-10 by comparing their PXRD profiles.

In yet another aspect, the invention features a crystalline form of Compound I which has characteristic peaks in the powder X-ray diffraction (PXRD) pattern at values of two theta (° 2θ) of 3.78, 4.09, 8.19, 9.15, 10.42, 13.02, 13.50, 18.45, 19.48, and 20.86.

In yet another aspect, the invention features a crystalline form of Compound I which has characteristic peaks in the powder X-ray diffraction (PXRD) pattern at values of two theta (° 2θ) of 3.78, 4.09, 6.92, 8.19, 9.15, 10.12, 10.42, 12.30, 13.02, 13.50, 14.77, 16.20, 16.97, 18.12, 18.45, 19.48, 20.86, 24.24, 24.79, and 25.97.

In yet another aspect, the invention features a crystalline form of Compound I which has characteristic peaks in the powder X-ray diffraction (PXRD) pattern at values of two theta (° 2θ) of 3.78, 4.09, 6.72, 6.92, 8.19, 9.15, 9.84, 10.12, 10.42, 10.72, 11.66, 12.30, 13.02, 13.50, 14.77, 15.26, 15.62, 16.20, 16.97, 17.27, 17.55, 18.12, 18.45, 19.48, 19.90, 20.37, 20.61, 20.86, 21.99, 22.25, 22.72, 24.24, 24.79, 25.97, 26.88, 27.42, 27.81, and 30.23.

Figure 2:
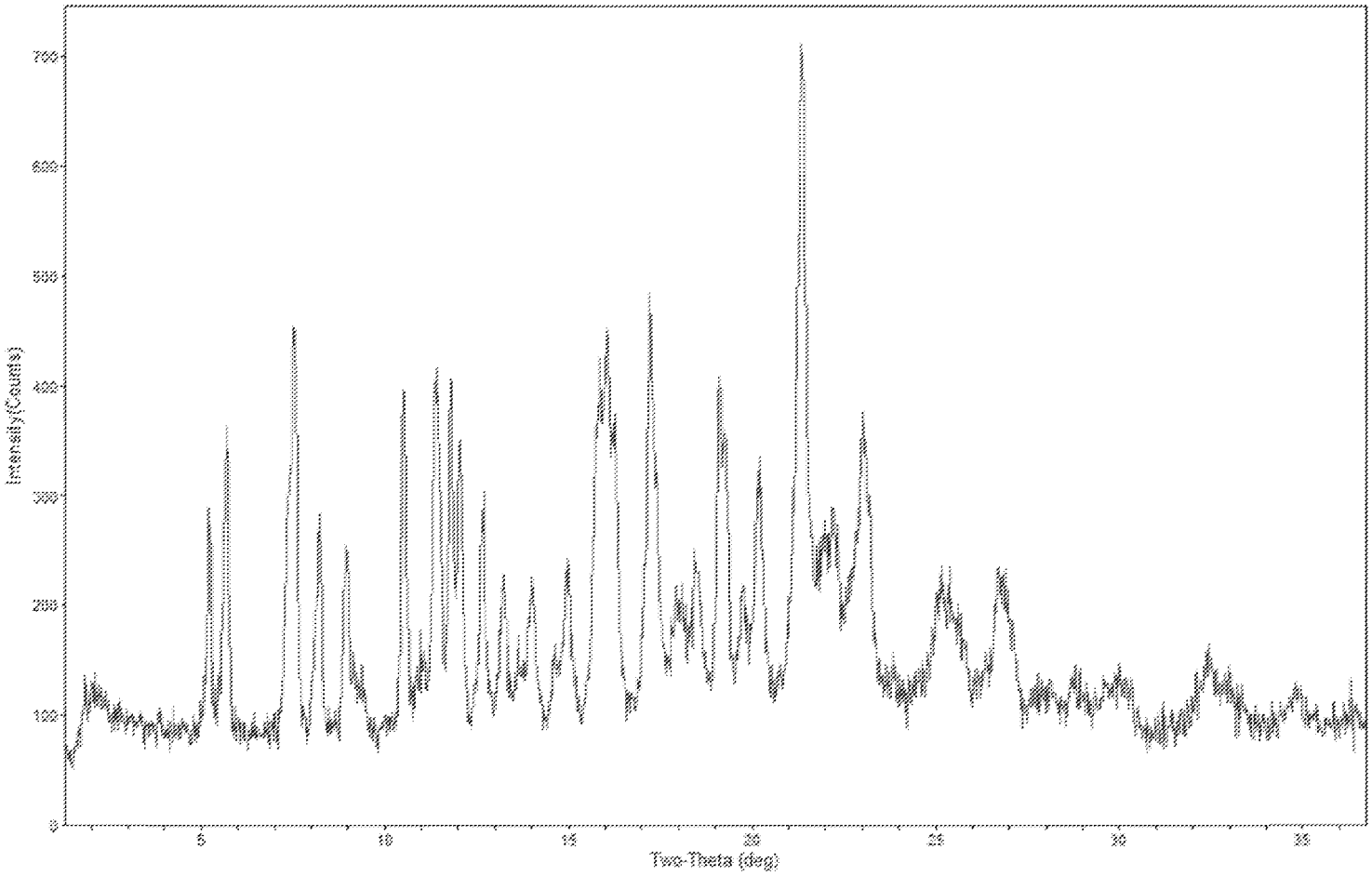
FIG. 2 depicts experimental PXRD pattern of Compound I Pattern B.

In yet another aspect, the invention features a crystalline form of Compound I which has characteristic peaks in the powder X-ray diffraction (PXRD) pattern as shown in FIG. 2.

In yet another aspect, the invention features a crystalline form of Compound I which has characteristic peaks in the powder X-ray diffraction (PXRD) pattern at values of two theta (° 2θ) as shown in Table 2.

In yet another aspect, the invention features a crystalline form of Compound I which has characteristic peaks in the powder X-ray diffraction (PXRD) pattern at values of two theta (° 2θ) of 5.70, 7.53, 10.51, 11.43, 11.80, 15.85, 17.23, 19.11, 21.37, and 23.00.

In yet another aspect, the invention features a crystalline form of Compound I which has characteristic peaks in the powder X-ray diffraction (PXRD) pattern at values of two theta (° 2θ) of 5.23, 5.70, 7.53, 8.24, 8.97, 10.51, 11.43, 11.80, 12.05, 12.69, 13.23, 14.97, 15.85, 17.23, 19.11, 20.20, 21.37, 21.99, 22.22, and 23.00.

In yet another aspect, the invention features a crystalline form of Compound I which has characteristic peaks in the powder X-ray diffraction (PXRD) pattern at values of two theta (° 2θ) of 5.23, 5.70, 7.53, 8.24, 8.97, 10.51, 11.43, 11.80, 12.05, 12.69, 13.23, 13.99, 14.97, 15.85, 17.23, 18.45, 19.11, 19.76, 20.20, 21.37, 21.99, 22.22, 23.00, 25.17, 25.43, 26.73, and 32.46.

Figure 3:
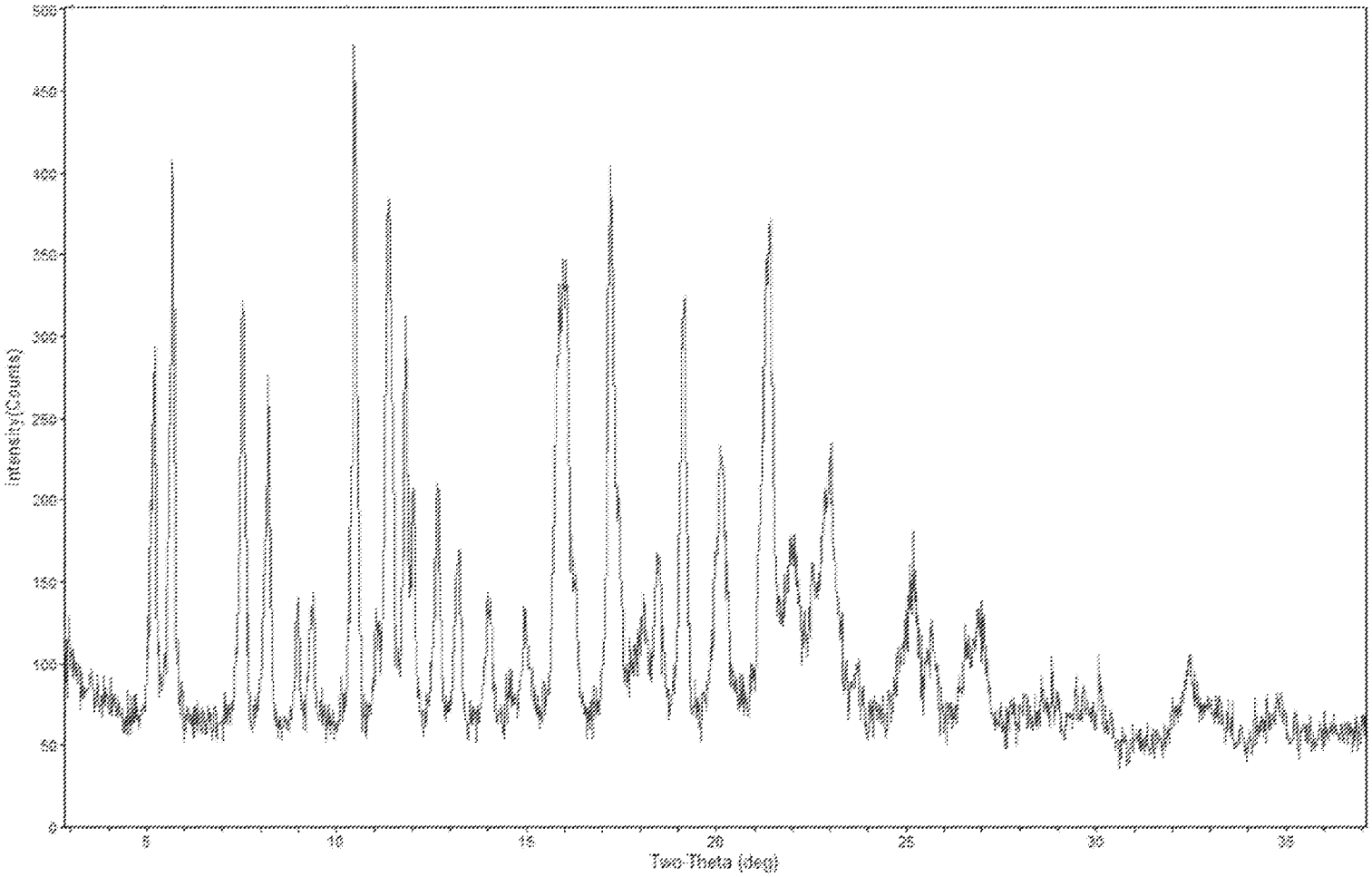
FIG. 3 describes experimental PXRD of Compound I Pattern B (MeOH-Diethyl ether solvate).

In yet another aspect, the invention features a crystalline form of Compound I which has characteristic peaks in the powder X-ray diffraction (PXRD) pattern as shown in FIG. 3.

In yet another aspect, the invention features a crystalline form of Compound I which has characteristic peaks in the powder X-ray diffraction (PXRD) pattern at values of two theta (° 2θ) as shown in Table 3.

In yet another aspect, the invention features a crystalline form of Compound I which has characteristic peaks in the powder X-ray diffraction (PXRD) pattern at values of two theta (° 2θ) of 5.22, 5.69, 7.55, 10.49, 11.38, 11.84, 15.99, 17.23, 19.18, and 21.41.

In yet another aspect, the invention features a crystalline form of Compound I which has characteristic peaks in the powder X-ray diffraction (PXRD) pattern at values of two theta (° 2θ) of 5.22, 5.69, 7.55, 8.21, 9.40, 10.49, 11.38, 11.84, 12.04, 12.67, 13.24, 15.99, 17.23, 19.18, 20.15, 21.41, 22.10, 22.53, 23.02, and 25.19.

In yet another aspect, the invention features a crystalline form of Compound I which has characteristic peaks in the powder X-ray diffraction (PXRD) pattern at values of two theta (° 2θ) of 5.22, 5.69, 7.55, 8.21, 8.99, 9.40, 10.49, 11.07, 11.38, 11.84, 12.04, 12.67, 13.24, 13.99, 14.96, 15.99, 17.23, 18.10, 18.47, 19.18, 20.15, 21.41, 22.10, 22.53, 23.02, 25.19, 25.69, 26.57, 26.98, 30.09, and 32.45.

Figure 4:
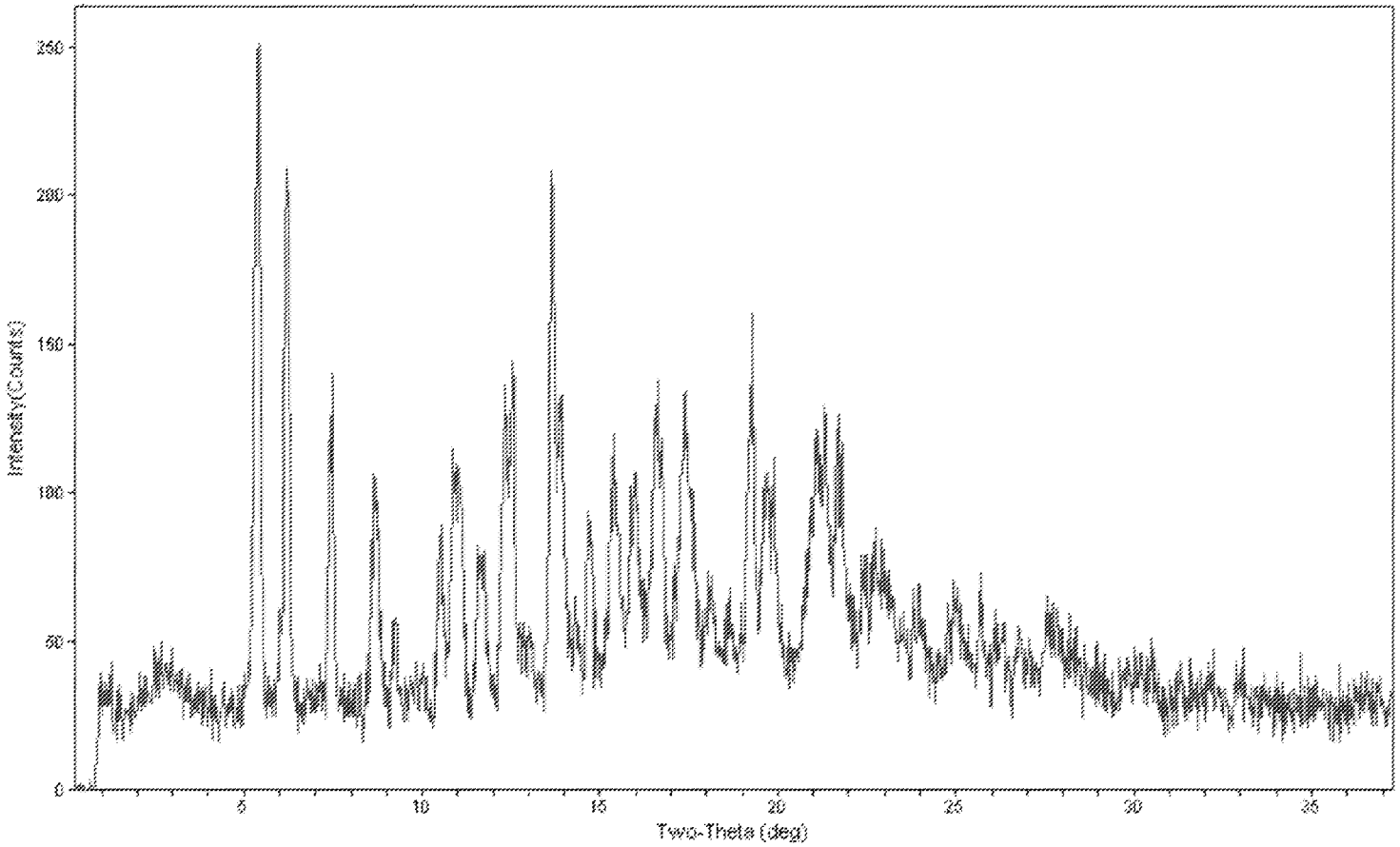
FIG. 4 shows experimental PXRD of Compound I Pattern C (anhydrate).

In yet another aspect, the invention features a crystalline form of Compound I which has characteristic peaks in the powder X-ray diffraction (PXRD) pattern as shown in FIG. 4.

In yet another aspect, the invention features a crystalline form of Compound I which has characteristic peaks in the powder X-ray diffraction (PXRD) pattern at values of two theta (° 2θ) as shown in Table 4.

In yet another aspect, the invention features a crystalline form of Compound I which has characteristic peaks in the powder X-ray diffraction (PXRD) pattern at values of two theta (° 2θ) of 5.43, 6.24, 7.53, 10.91, 12.34, 12.57, 13.67, 13.94, 17.44, and 19.30.

In yet another aspect, the invention features a crystalline form of Compound I which has characteristic peaks in the powder X-ray diffraction (PXRD) pattern at values of two theta (° 2θ) of 5.43, 6.24, 7.53, 8.68, 10.58, 10.91, 12.34, 12.57, 13.67, 13.94, 14.71, 15.40, 15.99, 16.64, 17.44, 19.30, 19.70, 21.10, 21.33, and 21.72.

In yet another aspect, the invention features a crystalline form of Compound I which has characteristic peaks in the powder X-ray diffraction (PXRD) pattern at values of two theta (° 2θ) of 5.43, 6.24, 7.53, 8.68, 9.28, 10.58, 10.91, 11.65, 12.34, 12.57, 13.67, 13.94, 14.71, 15.40, 15.99, 16.64, 17.44, 19.30, 19.70, 21.10, 21.33, 21.72, and 22.78.

Figure 5:
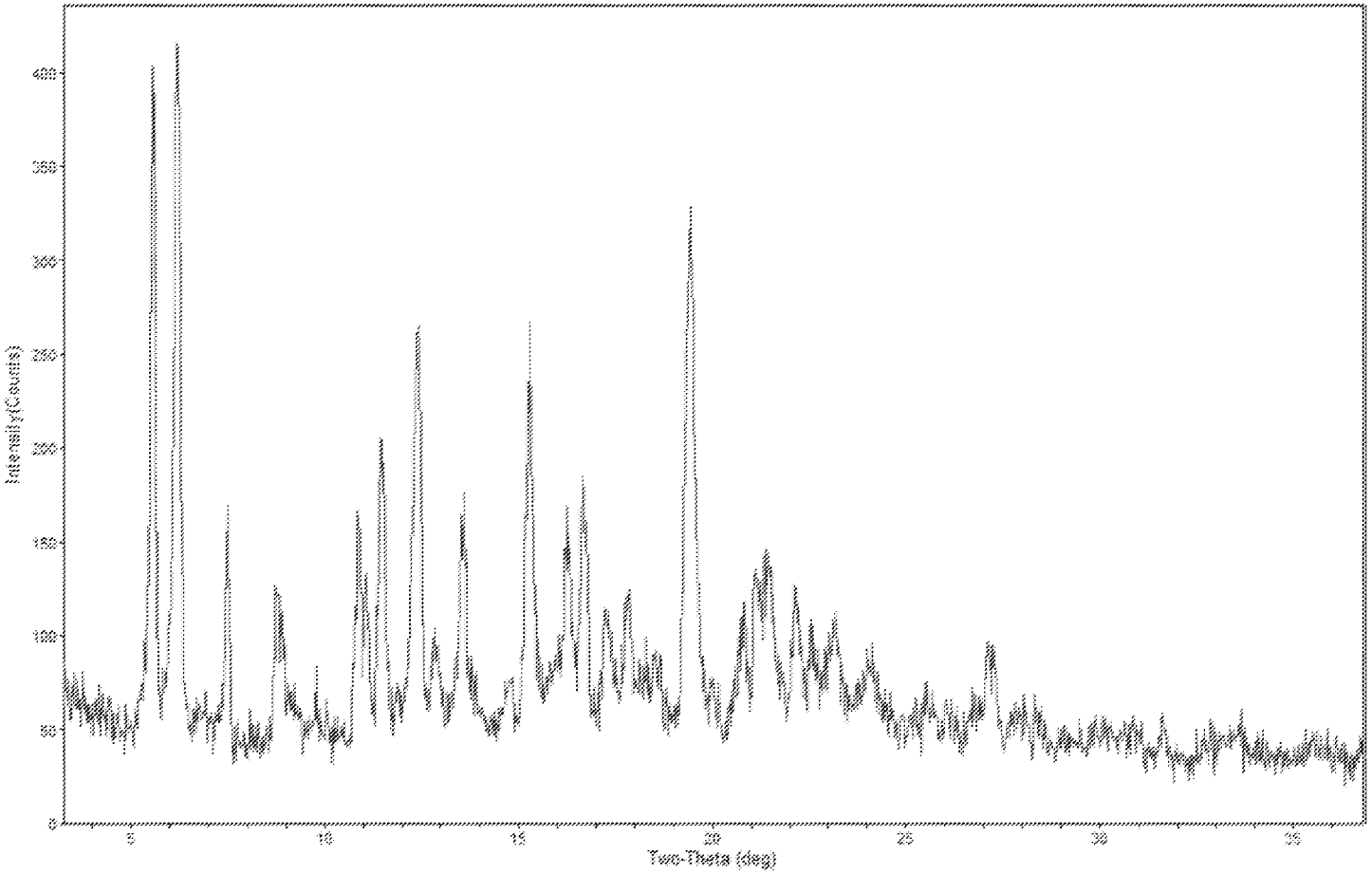
FIG. 5 illustrates experimental PXRD of Compound I Pattern C (MTBE solvate).

In yet another aspect, the invention features a crystalline form of Compound I which has characteristic peaks in the powder X-ray diffraction (PXRD) pattern as shown in FIG. 5.

In yet another aspect, the invention features a crystalline form of Compound I which has characteristic peaks in the powder X-ray diffraction (PXRD) pattern at values of two theta (° 2θ) as shown in Table 5.

In yet another aspect, the invention features a crystalline form of Compound I which has characteristic peaks in the powder X-ray diffraction (PXRD) pattern at values of two theta (° 2θ) of 5.57, 6.19, 7.50, 10.86, 11.46, 12.42, 13.59, 15.28, 16.66, and 19.44.

In yet another aspect, the invention features a crystalline form of Compound I which has characteristic peaks in the powder X-ray diffraction (PXRD) pattern at values of two theta (° 2θ) of 5.57, 6.19, 7.50, 8.75, 10.86, 11.08, 11.46, 12.42, 13.59, 15.28, 16.26, 16.66, 17.25, 17.87, 19.44, 20.80, 21.13, 21.39, 22.15, and 27.12.

In yet another aspect, the invention features a crystalline form of Compound I which has characteristic peaks in the powder X-ray diffraction (PXRD) pattern at values of two theta (° 2θ) of 5.57, 6.19, 7.50, 8.75, 10.86, 11.08, 11.46, 12.42, 12.84, 13.59, 15.28, 16.26, 16.66, 17.25, 17.87, 19.44, 20.80, 21.13, 21.39, 22.15, 23.17, 24.15, and 27.12.

Figure 6:
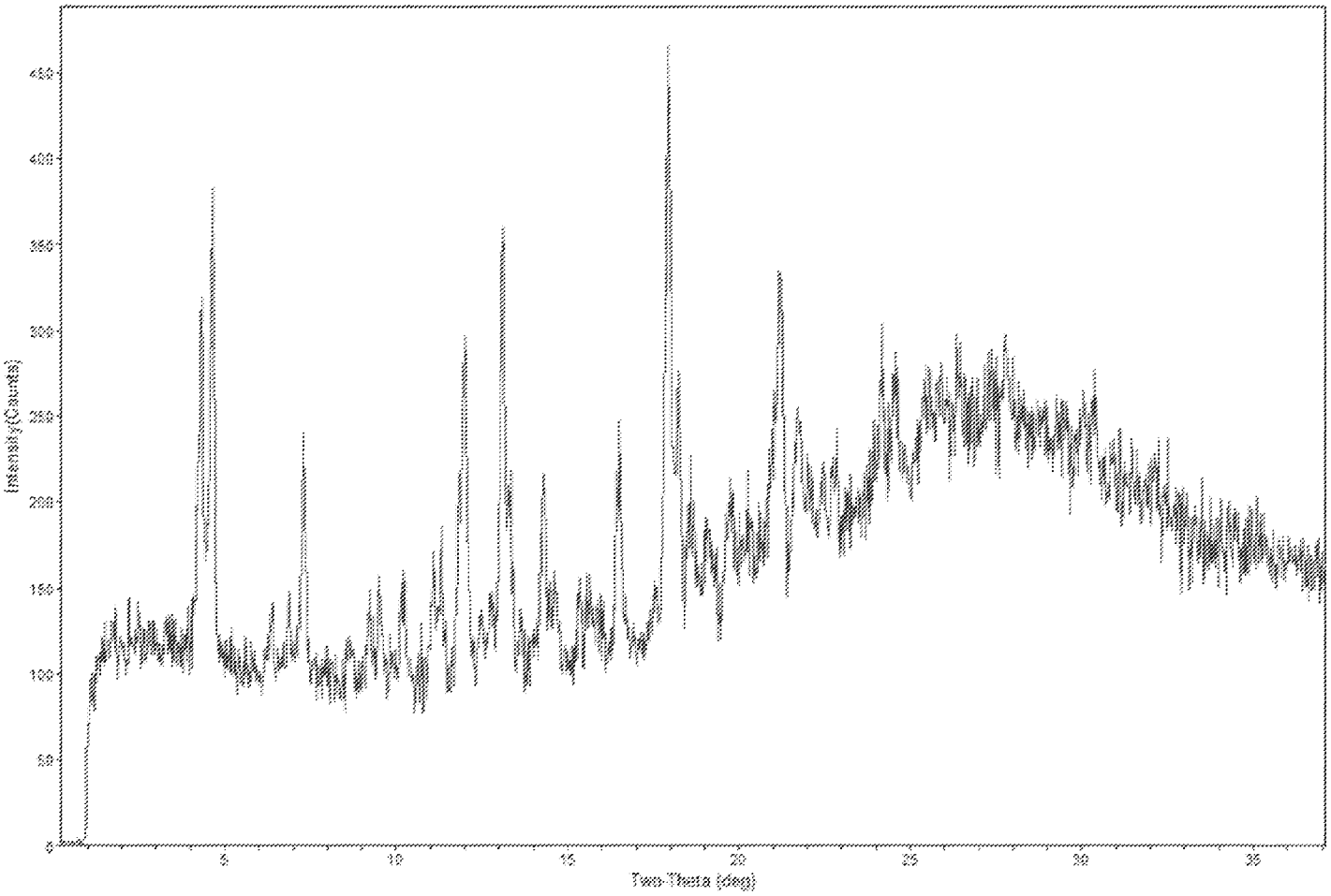
FIG. 6 depicts experimental PXRD of Compound I Pattern D (from EtOH/$H_2O$).

In yet another aspect, the invention features a crystalline form of Compound I which has characteristic peaks in the powder X-ray diffraction (PXRD) pattern as shown in FIG. 6.

In yet another aspect, the invention features a crystalline form of Compound I which has characteristic peaks in the powder X-ray diffraction (PXRD) pattern at values of two theta (° 2θ) as shown in Table 6.

In yet another aspect, the invention features a crystalline form of Compound I which has characteristic peaks in the powder X-ray diffraction (PXRD) pattern at values of two theta (° 2θ) of 4.35, 4.68, 7.33, 12.01, 13.13, 13.35, 16.54, 17.96, 18.26, and 21.21.

In yet another aspect, the invention features a crystalline form of Compound I which has characteristic peaks in the powder X-ray diffraction (PXRD) pattern at values of two theta (° 2θ) of 4.35, 4.68, 6.41, 7.33, 9.54, 10.26, 11.13, 11.34, 12.01, 13.13, 13.35, 14.33, 16.54, 17.96, 18.26, 18.60, 19.77, 21.21, 21.75, and 24.19.

In yet another aspect, the invention features a crystalline form of Compound I which has characteristic peaks in the powder X-ray diffraction (PXRD) pattern at values of two theta (° 2θ) of 4.35, 4.68, 6.41, 6.92, 7.33, 9.25, 9.54, 10.26, 11.13, 11.34, 12.01, 13.13, 13.35, 14.33, 14.65, 15.36, 16.54, 17.96, 18.26, 18.60, 19.05, 19.77, 21.21, 21.75, and 24.19.

Figure 7:
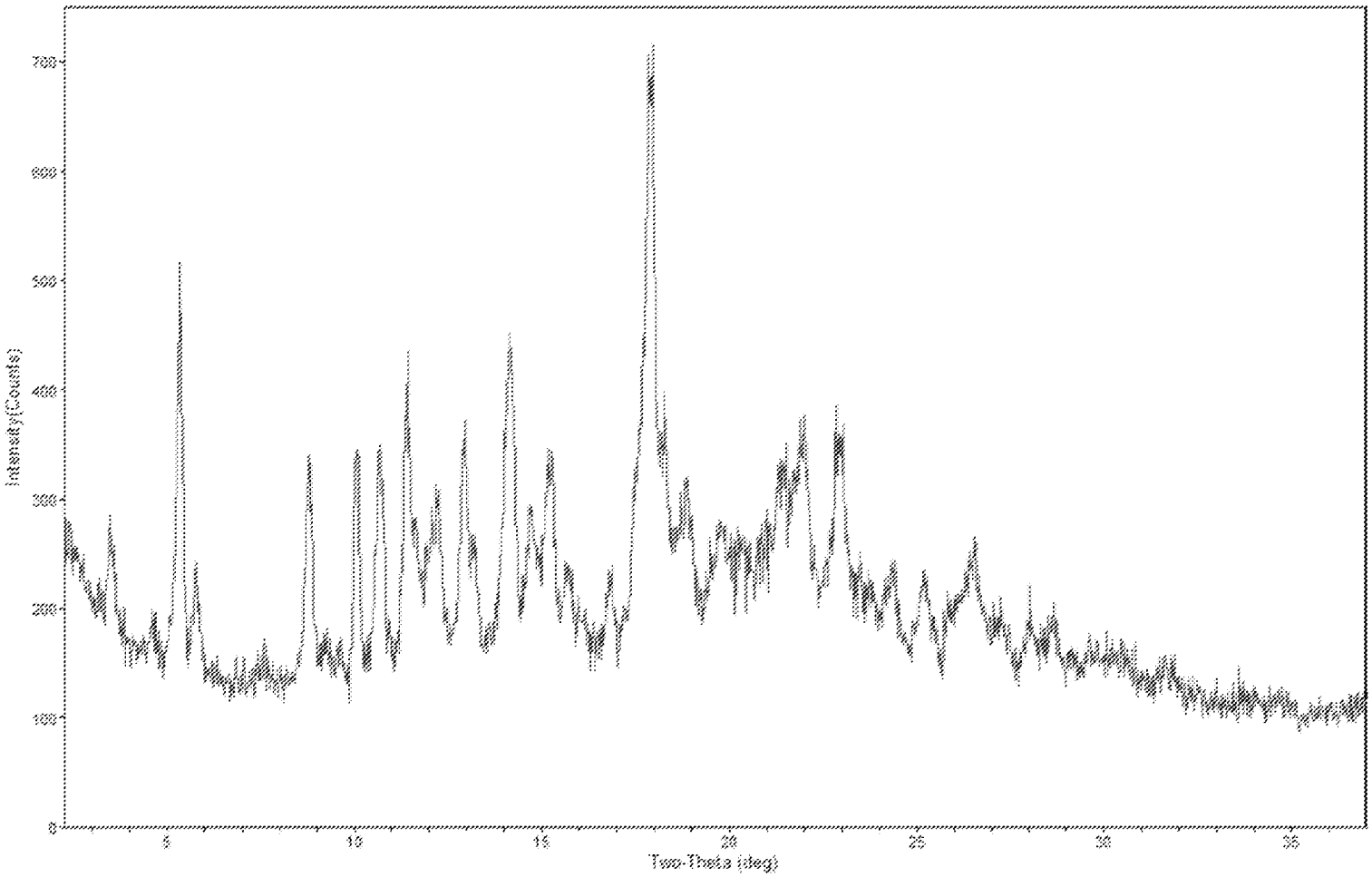
FIG. 7 shows experimental PXRD of Compound I Pattern E (hydrate).

In yet another aspect, the invention features a crystalline form of Compound I which has characteristic peaks in the powder X-ray diffraction (PXRD) pattern as shown in FIG. 7.

In yet another aspect, the invention features a crystalline form of Compound I which has characteristic peaks in the powder X-ray diffraction (PXRD) pattern at values of two theta (° 2θ) as shown in Table 7.

In yet another aspect, the invention features a crystalline form of Compound I which has characteristic peaks in the powder X-ray diffraction (PXRD) pattern at values of two theta (° 2θ) of 5.36, 8.81, 10.09, 10.69, 11.43, 12.95, 14.14, 17.96, 18.28, and 22.88.

In yet another aspect, the invention features a crystalline form of Compound I which has characteristic peaks in the powder X-ray diffraction (PXRD) pattern at values of two theta (° 2θ) of 3.50, 5.36, 8.81, 10.09, 10.69, 11.43, 12.19, 12.95, 14.14, 14.72, 15.18, 17.53, 17.96, 18.28, 18.86, 21.36, 22.01, 22.88, 26.54, and 28.04.

In yet another aspect, the invention features a crystalline form of Compound I which has characteristic peaks in the powder X-ray diffraction (PXRD) pattern at values of two theta (° 2θ) of 3.50, 4.61, 5.36, 5.79, 7.61, 8.81, 10.09, 10.69, 11.43, 12.19, 12.95, 14.14, 14.72, 15.18, 15.64, 16.87, 17.53, 17.96, 18.28, 18.86, 19.76, 21.36, 22.01, 22.88, 24.42, 25.20, 26.54, 28.04, and 28.65.

Figure 8:
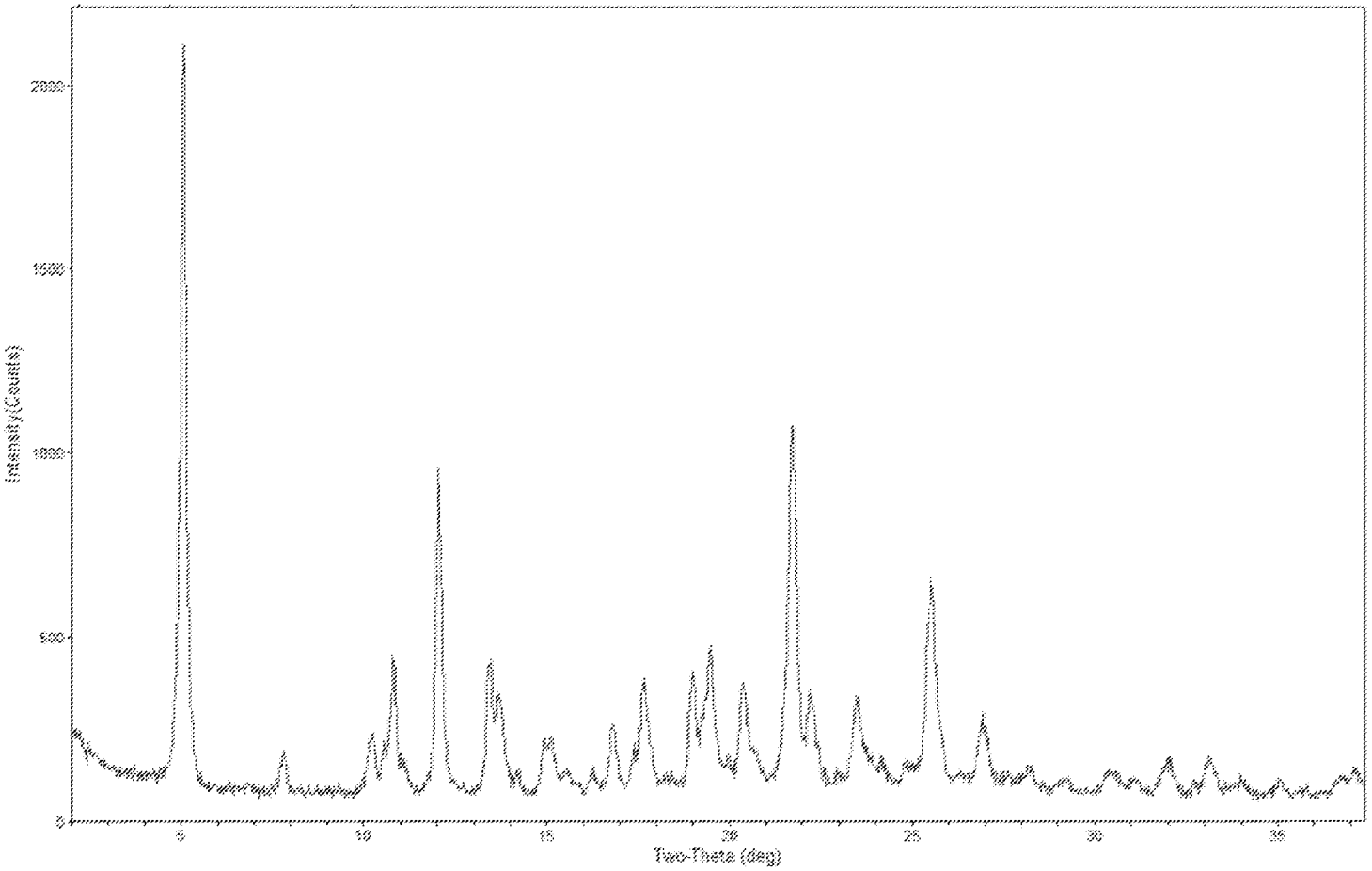
FIG. 8 describes experimental PXRD of Compound I ACN solvate (Pattern F or Form II).

In yet another aspect, the invention features a crystalline form of Compound I which has characteristic peaks in the powder X-ray diffraction (PXRD) pattern as shown in FIG. 8.

In yet another aspect, the invention features a crystalline form of Compound I which has characteristic peaks in the powder X-ray diffraction (PXRD) pattern at values of two theta (° 2θ) as shown in Table 8.

In yet another aspect, the invention features a crystalline form of Compound I which has characteristic peaks in the powder X-ray diffraction (PXRD) pattern at values of two theta (° 2θ) of 5.08, 10.81, 12.05, 13.47, 13.68, 17.68, 19.02, 19.48, 21.73, and 25.53.

In yet another aspect, the invention features a crystalline form of Compound I which has characteristic peaks in the powder X-ray diffraction (PXRD) pattern at values of two theta (° 2θ) of 5.08, 7.82, 10.27, 10.81, 12.05, 13.47, 13.68, 14.95, 16.81, 17.68, 19.02, 19.48, 20.36, 21.73, 22.24, 23.48, 25.53, 26.93, 32.01, and 33.12.

In yet another aspect, the invention features a crystalline form of Compound I which has characteristic peaks in the powder X-ray diffraction (PXRD) pattern at values of two theta (° 2θ) of 5.08, 7.82, 10.27, 10.81, 11.11, 12.05, 13.47, 13.68, 14.95, 15.57, 16.28, 16.81, 17.68, 19.02, 19.48, 20.36, 21.73, 22.24, 23.48, 24.16, 25.53, 26.93, 28.26, 30.41, 31.07, 32.01, 33.12, and 35.04.

Figure 9:
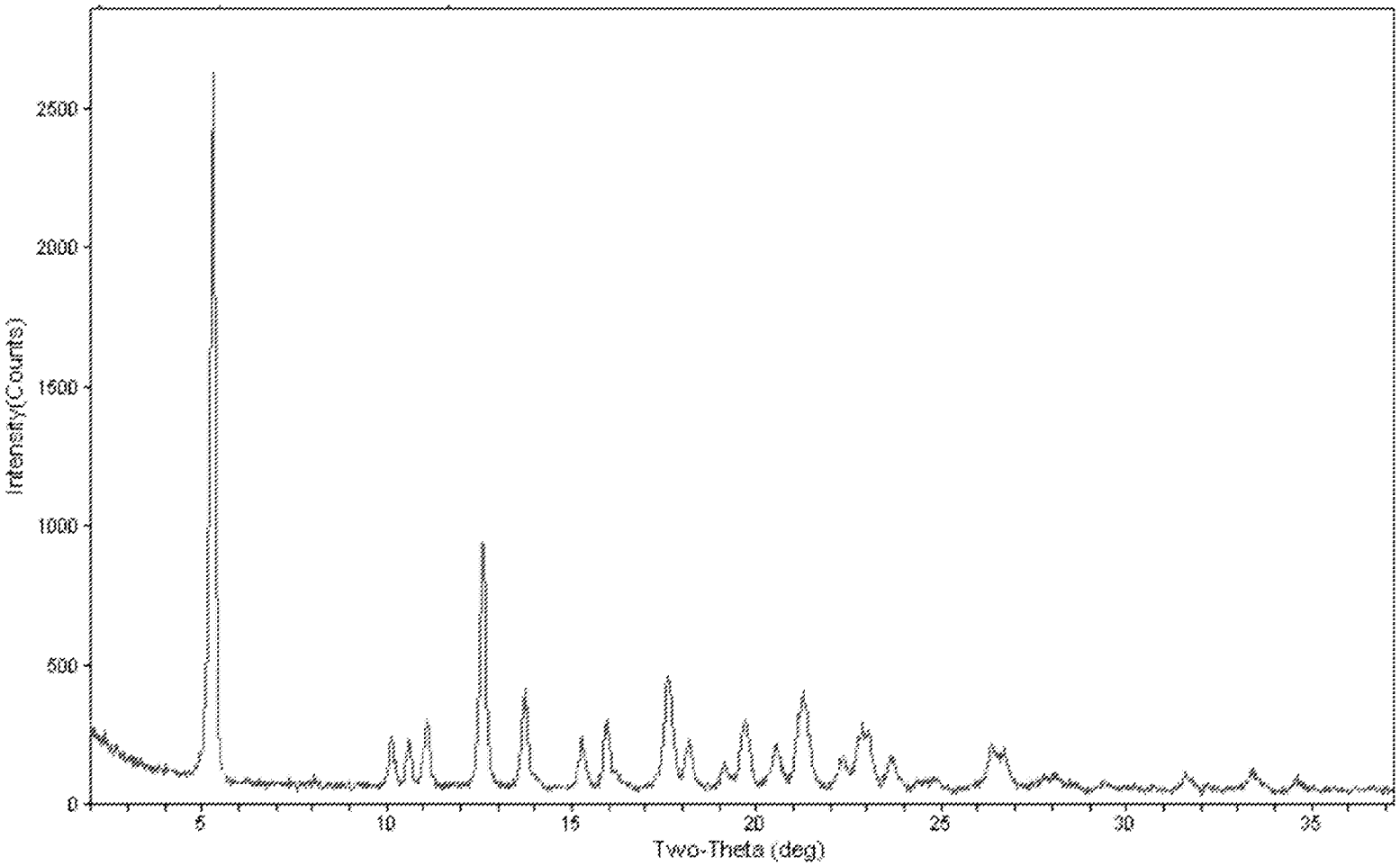
FIG. 9 shows experimental PXRD of Compound I anhydrate (Pattern G or Form III).

In yet another aspect, the invention features a crystalline form of Compound I which has characteristic peaks in the powder X-ray diffraction (PXRD) pattern as shown in FIG. 9.

In yet another aspect, the invention features a crystalline form of Compound I which has characteristic peaks in the powder X-ray diffraction (PXRD) pattern at values of two theta (° 2θ) as shown in Table 9.

In yet another aspect, the invention features a crystalline form of Compound I which has characteristic peaks in the powder X-ray diffraction (PXRD) pattern at values of two theta (° 2θ) of 5.31, 11.11, 12.60, 13.75, 15.29, 15.96, 17.62, 19.71, 21.30, and 22.88.

In yet another aspect, the invention features a crystalline form of Compound I which has characteristic peaks in the powder X-ray diffraction (PXRD) pattern at values of two theta (° 2θ) of 5.31, 10.16, 10.62, 11.11, 12.60, 13.75, 15.29, 15.96, 17.62, 18.19, 19.16, 19.71, 20.58, 21.30, 22.40, 22.88, 23.66, 26.40, 26.74, and 33.46.

In yet another aspect, the invention features a crystalline form of Compound I which has characteristic peaks in the powder X-ray diffraction (PXRD) pattern at values of two theta (° 2θ) of 5.31, 10.16, 10.62, 11.11, 12.60, 13.75, 15.29, 15.96, 17.62, 18.19, 19.16, 19.71, 20.58, 21.30, 22.40, 22.88, 23.66, 26.40, 26.74, 28.12, 31.62, and 33.46.

Figure 10:
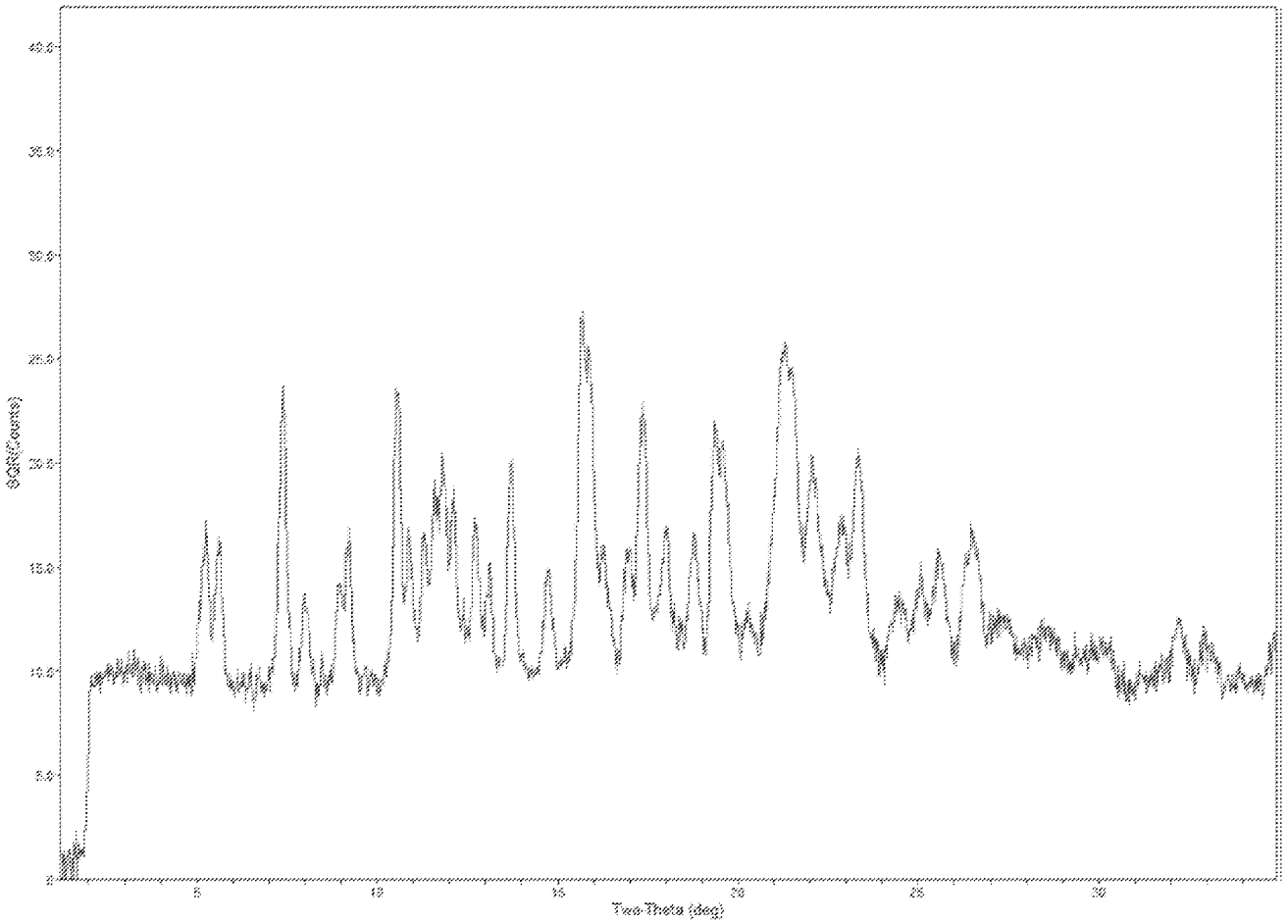
FIG. 10 depicts experimental PXRD of Compound I di-n-butyl ether solvate (Pattern H).

In yet another aspect, the invention features a crystalline form of Compound I which has characteristic peaks in the powder X-ray diffraction (PXRD) pattern as shown in FIG. 10.

In yet another aspect, the invention features a crystalline form of Compound I which has characteristic peaks in the powder X-ray diffraction (PXRD) pattern at values of two theta (° 2θ) as shown in Table 10.

In yet another aspect, the invention features a crystalline form of Compound I which has characteristic peaks in the powder X-ray diffraction (PXRD) pattern at values of two theta (° 2θ) of 7.42, 10.57, 11.84, 13.74, 15.72, 17.36, 19.38, 21.34, 22.07, and 23.36.

In yet another aspect, the invention features a crystalline form of Compound I which has characteristic peaks in the powder X-ray diffraction (PXRD) pattern at values of two theta (° 2θ) of 5.28, 5.65, 7.42, 9.26, 10.57, 10.90, 11.31, 11.84, 12.15, 12.73, 13.74, 15.72, 17.36, 18.04, 19.38, 21.34, 22.07, 22.90, 23.36, and 26.49.

In yet another aspect, the invention features a crystalline form of Compound I which has characteristic peaks in the powder X-ray diffraction (PXRD) pattern at values of two theta (° 2θ) of 5.28, 5.65, 7.42, 8.02, 8.94, 9.26, 10.57, 10.90, 11.31, 11.84, 12.15, 12.73, 13.14, 13.74, 14.78, 15.72, 16.32, 16.95, 17.36, 18.04, 18.81, 19.38, 21.34, 22.07, 22.90, 23.36, 24.50, 25.13, 25.59, 26.49, 32.24, and 32.93.

As used herein, PXRD data can be collected using a G3000 diffractometer (Inel Corp., Artenay, France) equipped with a curved position-sensitive detector and parallel-beam optics. The diffractometer is operated with a copper anode tube (1.5 kW fine focus) at 40 kV and 30 mA. An incident-beam germanium monochromator provides monochromatic Cu-$K_\alpha$ radiation, which has a wavelength of 1.54178 Å. The diffractometer is calibrated using the attenuated direct beam at one-degree intervals. Calibration is checked using a silicon powder line position reference standard (NIST 640c). The instrument is computer-controlled using Symphonix software (Inel Corp., Artenay, France) and the data are analyzed using Jade software (version 6.5, Materials Data, Inc., Livermore, Calif.). The sample can be loaded onto an aluminum sample holder and leveled with a glass slide. PXRD peak position measurements are typically ±0.2 degrees two-theta (° 2θ).

In another aspect, the present invention features a crystalline form described above which is substantially pure. As used herein, the term "substantially pure", when used in reference to a given crystalline form, refers to the crystalline form which is at least about 90% pure. This means that the crystalline form does not contain more than about 10% of any other form of Compound I. More preferably, the term "substantially pure" refers to a crystalline form of Compound I which is at least about 95% pure. This means that the crystalline form of Compound I does not contain more than about 5% of any other form of Compound I. Even more preferably, the term "substantially pure" refers to a crystalline form of Compound I which is at least about 97% pure. This means that the crystalline form of Compound I does not to contain more than about 3% of any other form of Compound I.

In one embodiment, the present invention feature a crystalline form of Compound I which has characteristic peaks in the powder X-ray diffraction (PXRD) pattern as shown in FIG. 1 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) as shown in Table 1 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 3.78, 4.09, 8.19, 9.15, 10.42, 13.02, 13.50, 18.45, 19.48, and 20.86, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 3.78, 4.09, 6.92, 8.19, 9.15, 10.12, 10.42, 12.30, 13.02, 13.50, 14.77, 16.20, 16.97, 18.12, 18.45, 19.48, 20.86, 24.24, 24.79, and 25.97, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 3.78, 4.09, 6.72, 6.92, 8.19, 9.15, 9.84, 10.12, 10.42, 10.72, 11.66, 12.30, 13.02, 13.50, 14.77, 15.26, 15.62, 16.20, 16.97, 17.27, 17.55, 18.12, 18.45, 19.48, 19.90, 20.37, 20.61, 20.86, 21.99, 22.25, 22.72, 24.24, 24.79, 25.97, 26.88, 27.42, 27.81, and 30.23, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 2 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 2 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.70, 7.53, 10.51, 11.43, 11.80, 15.85, 17.23, 19.11, 21.37, and 23.00, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.23, 5.70, 7.53, 8.24, 8.97, 10.51, 11.43, 11.80, 12.05, 12.69, 13.23, 14.97, 15.85, 17.23, 19.11, 20.20, 21.37, 21.99, 22.22, and 23.00, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.23, 5.70, 7.53, 8.24, 8.97, 10.51, 11.43, 11.80, 12.05, 12.69, 13.23, 13.99, 14.97, 15.85, 17.23, 18.45, 19.11, 19.76, 20.20, 21.37, 21.99, 22.22, 23.00, 25.17, 25.43, 26.73, and 32.46, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 3 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 3 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.22, 5.69, 7.55, 10.49, 11.38, 11.84, 15.99, 17.23, 19.18, and 21.41, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.22, 5.69, 7.55, 8.21, 9.40, 10.49, 11.38, 11.84, 12.04, 12.67, 13.24, 15.99, 17.23, 19.18, 20.15, 21.41, 22.10, 22.53, 23.02, and 25.19, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.22, 5.69, 7.55, 8.21, 8.99, 9.40, 10.49, 11.07, 11.38, 11.84, 12.04, 12.67, 13.24, 13.99, 14.96, 15.99, 17.23, 18.10, 18.47, 19.18, 20.15, 21.41, 22.10, 22.53, 23.02, 25.19, 25.69, 26.57, 26.98, 30.09, and 32.45, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 4 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 4 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.43, 6.24, 7.53, 10.91, 12.34, 12.57, 13.67, 13.94, 17.44, and 19.30, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.43, 6.24, 7.53, 8.68, 10.58, 10.91, 12.34, 12.57, 13.67, 13.94, 14.71, 15.40, 15.99, 16.64, 17.44, 19.30, 19.70, 21.10, 21.33, and 21.72, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.43, 6.24, 7.53, 8.68, 9.28, 10.58, 10.91, 11.65, 12.34, 12.57, 13.67, 13.94, 14.71, 15.40, 15.99, 16.64, 17.44, 19.30, 19.70, 21.10, 21.33, 21.72, and 22.78, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 5 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 5 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.57, 6.19, 7.50, 10.86, 11.46, 12.42, 13.59, 15.28, 16.66, and 19.44, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.57, 6.19, 7.50, 8.75, 10.86, 11.08, 11.46, 12.42, 13.59, 15.28, 16.26, 16.66, 17.25, 17.87, 19.44, 20.80, 21.13, 21.39, 22.15, and 27.12, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.57, 6.19, 7.50, 8.75, 10.86, 11.08, 11.46, 12.42, 12.84, 13.59, 15.28, 16.26, 16.66, 17.25, 17.87, 19.44, 20.80, 21.13, 21.39, 22.15, 23.17, 24.15, and 27.12, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 6 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 6 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 4.35, 4.68, 7.33, 12.01, 13.13, 13.35, 16.54, 17.96, 18.26, and 21.21, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 4.35, 4.68, 6.41, 7.33, 9.54, 10.26, 11.13, 11.34, 12.01, 13.13, 13.35, 14.33, 16.54, 17.96, 18.26, 18.60, 19.77, 21.21, 21.75, and 24.19, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 4.35, 4.68, 6.41, 6.92, 7.33, 9.25, 9.54, 10.26, 11.13, 11.34, 12.01, 13.13, 13.35, 14.33, 14.65, 15.36, 16.54, 17.96, 18.26, 18.60, 19.05, 19.77, 21.21, 21.75, and 24.19, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 7 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 7 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.36, 8.81, 10.09, 10.69, 11.43, 12.95, 14.14, 17.96, 18.28, and 22.88, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 3.50, 5.36, 8.81, 10.09, 10.69, 11.43, 12.19, 12.95, 14.14, 14.72, 15.18, 17.53, 17.96, 18.28, 18.86, 21.36, 22.01, 22.88, 26.54, and 28.04, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 3.50, 4.61, 5.36, 5.79, 7.61, 8.81, 10.09, 10.69, 11.43, 12.19, 12.95, 14.14, 14.72, 15.18, 15.64, 16.87, 17.53, 17.96, 18.28, 18.86, 19.76, 21.36, 22.01, 22.88, 24.42, 25.20, 26.54, 28.04, and 28.65, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 8 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 8 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.08, 10.81, 12.05, 13.47, 13.68, 17.68, 19.02, 19.48, 21.73, and 25.53, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.08, 7.82, 10.27, 10.81, 12.05, 13.47, 13.68, 14.95, 16.81, 17.68, 19.02, 19.48, 20.36, 21.73, 22.24, 23.48, 25.53, 26.93, 32.01, and 33.12, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.08, 7.82, 10.27, 10.81, 11.11, 12.05, 13.47, 13.68, 14.95, 15.57, 16.28, 16.81, 17.68, 19.02, 19.48, 20.36, 21.73, 22.24, 23.48, 24.16, 25.53, 26.93, 28.26, 30.41, 31.07, 32.01, 33.12, and 35.04, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 9 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 9 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.31, 11.11, 12.60, 13.75, 15.29, 15.96, 17.62, 19.71, 21.30, and 22.88, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.31, 10.16, 10.62, 11.11, 12.60, 13.75, 15.29, 15.96, 17.62, 18.19, 19.16, 19.71, 20.58, 21.30, 22.40, 22.88, 23.66, 26.40, 26.74, and 33.46, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.31, 10.16, 10.62, 11.11, 12.60, 13.75, 15.29, 15.96, 17.62, 18.19, 19.16, 19.71, 20.58, 21.30, 22.40, 22.88, 23.66, 26.40, 26.74, 28.12, 31.62, and 33.46, and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern as shown in FIG. 10 and which is substantially pure. For example the crystalline form can be at least 90% pure, preferably at least 95% pure, or more preferably at least 97%.

In yet another embodiment, the present invention feature a crystalline form of Compound I which has characteristic peaks in the powder X-ray diffraction (PXRD) pattern at values of two theta (° 2θ) as shown in Table 10 and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 7.42, 10.57, 11.84, 13.74, 15.72, 17.36, 19.38, 21.34, 22.07, and 23.36, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.28, 5.65, 7.42, 9.26, 10.57, 10.90, 11.31, 11.84, 12.15, 12.73, 13.74, 15.72, 17.36, 18.04, 19.38, 21.34, 22.07, 22.90, 23.36, and 26.49, and which is substantially pure. For example the crystalline form can be at least 90% pure, preferably at least 95% pure, or more preferably at least 97%.

In another embodiment, the present invention feature a crystalline form of Compound I which has characteristic peaks in the powder X-ray diffraction (PXRD) pattern at values of two theta (° 2θ) of 5.28, 5.65, 7.42, 8.02, 8.94, 9.26, 10.57, 10.90, 11.31, 11.84, 12.15, 12.73, 13.14, 13.74, 14.78, 15.72, 16.32, 16.95, 17.36, 18.04, 18.81, 19.38, 21.34, 22.07, 22.90, 23.36, 24.50, 25.13, 25.59, 26.49, 32.24, and 32.93, and which is substantially pure. For example the crystalline form can be at least 90% pure, preferably at least 95% pure, or more preferably at least 97%.

In yet another aspect, the present invention features processes of using a crystalline form of the invention to make a composition comprising Compound I. The processes comprise dissolving a crystalline form of the invention in a solvent.

Any crystalline form described herein, including any crystalline form described in any aspect, embodiment or example of this application, can be used in any process of the invention described herein.

In one embodiment, the solvent is a volatile solvent such as ethanol or methanol. A suitable excipient, such as a hydrophilic polymer described below or a sugar alcohol, can also be dissolved in the solvent. The solution thus produced can then be dried to remove the solvent, such as via spray drying, freeze drying or other solvent evaporization techniques, thereby creating a solid dispersion that comprises Compound I and the excipient. Preferably, Compound I is in an amorphous form in the solid dispersion. More preferably, the solid dispersion is a solid solution or a glassy solution. In many cases, a pharmaceutically acceptable surfactant described below can also be added to the solution prior to solvent removal; and as a result, the solid dispersion/solid solution/glass solution produced according to this embodiment also comprises the surfactant.

In another embodiment, the solvent is an excipient, such as a hydrophilic polymer described below or a sugar alcohol, in a molten or rubbery state. The crystalline form of Compound I dissolves in the molten or rubbery excipient. Heating may be used to facilitate the dissolving and mixing of the crystalline form of Compound I in the molten or rubbery excipient. Preferably, melt extrusion is used to dissolve and mix the crystalline form of Compound I in the excipient. A solution or melt thus produced can be cooled and solidified to form a solid dispersion that comprises Compound I and the excipient. Preferably, Compound I is in an amorphous form in the solid dispersion. More preferably, the solid dispersion is a solid solution or a glassy solution. The solid dispersion, solid solution or glassy solution can be milled, ground or granulated, and then compressed into a tablet or another suitable solid dosage form with or without other additives. The solid dispersion, solid solution or glassy solution can also be directly shaped or configured into a tablet or another suitable solid dosage form. In many cases, a pharmaceutically acceptable surfactant described below can be added to the solution or melt prior to solidification; and as a result, the solid dispersion/solid solution/glassy solution produced according to this embodiment also comprises the surfactant.

In yet another embodiment, both heating and a volatile solvent are used to dissolve a crystalline form of Compound I in a solution comprising a suitable excipient.

As used herein, the term "solid dispersion" defines a system in a solid state (as opposed to a liquid or gaseous state) comprising at least two components, wherein one component is dispersed throughout the other component or components. For example, an active ingredient or a combination of active ingredients can be dispersed in a matrix comprised of a pharmaceutically acceptable hydrophilic polymer(s) and a pharmaceutically acceptable surfactant(s). The term "solid dispersion" encompasses systems having small particles of one phase dispersed in another phase. When a solid dispersion of the components is such that the system is chemically and physically uniform or homogenous throughout or consists of one phase (as defined in thermodynamics), such a solid dispersion is called a "solid solution." A glassy solution is a solid solution in which a solute is dissolved in a glassy solvent.

Non-limiting examples of excipients suitable for use in a process of the invention include numerous hydrophilic polymers. Preferably, a hydrophilic polymer employed in a process of the invention has a $T_g$ of at least 50° C., more preferably at least 60° C., and highly preferably at least 80° C. including, but not limited to from, 80° C. to 180° C., or from 100° C. to 150° C. Methods for determining $T_g$ values of organic polymers are described in Introduction to Physical Polymer Science (2nd Edition by L. H. Sperling, published by John Wiley & Sons, Inc., 1992). The $T_g$ value can be calculated as the weighted sum of the $T_g$ values for homopolymers derived from each of the individual monomers, i.e., the polymer $T_g=\Sigma W_i \cdot X_i$ where $W_i$ is the weight percent of monomer i in the organic polymer, and X, is the $T_g$ value for the homopolymer derived from monomer i. $T_g$ values for the homopolymers may be taken from Polymer Handbook (2nd Edition by J. Brandrup and E. H. Immergut, Editors, published by John Wiley & Sons, Inc., 1975). Hydrophilic polymers with a $T_g$ as described above may allow for the preparation of solid dispersions that are mechanically stable and, within ordinary temperature ranges, sufficiently temperature stable so that the solid dispersions may be used as dosage forms without further processing or be compacted to tablets with only a small amount of tabletting aids. Hydrophilic polymers having a $T_g$ of below 50° C. may also be used.

Preferably, a hydrophilic polymer employed in the present invention is water-soluble. A solid composition of the present invention can also comprise poorly water-soluble or water-insoluble polymer or polymers, such as cross-linked polymers. A hydrophilic polymer comprised in a solid composition of the present invention preferably has an apparent viscosity, when dissolved at 20° C. in an aqueous solution at 2% (w/v), of 1 to 5000 mPa·s., and more preferably of 1 to 700 mPa·s, and most preferably of 5 to 100 mPa·s.

Hydrophilic polymers suitable for use in a process of the invention include, but are not limited to, homopolymers or copolymers of N-vinyl lactams, such as homopolymers or copolymers of N-vinyl pyrrolidone (e.g., polyvinylpyrrolidone (PVP), or copolymers of N-vinyl pyrrolidone and vinyl acetate or vinyl propionate); cellulose esters or cellulose ethers, such as alkylcelluloses (e.g., methylcellulose or ethylcellulose), hydroxyalkylcelluloses (e.g., hydroxypropylcellulose), hydroxyalkylalkylcelluloses (e.g., hydroxypropylmethylcellulose), and cellulose phthalates or succinates (e.g., cellulose acetate phthalate and hydroxypropylmethylcellulose phthalate, hydroxypropylmethylcellulose succinate, or hydroxypropylmethylcellulose acetate succinate); high molecular polyalkylene oxides, such as polyethylene oxide, polypropylene oxide, and copolymers of ethylene oxide and propylene oxide; polyacrylates or polymethacrylates, such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), and poly(hydroxyalkyl methacrylates); polyacrylamides; vinyl acetate polymers, such as copolymers of vinyl acetate and crotonic acid, and partially hydrolyzed polyvinyl acetate (also referred to as partially saponified "polyvinyl alcohol"); polyvinyl alcohol; oligo- or polysaccharides, such as carrageenans, galactomannans, and xanthan gum; polyhydroxyalkylacrylates; polyhydroxyalkyl-methacrylates; copolymers of methyl methacrylate and acrylic acid; polyethylene glycols (PEGs); or any mixture thereof.

Non-limiting examples of preferred hydrophilic polymers for use in a process of the invention include polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, poloxamer 124, poloxamer 188, poloxamer 237, poloxamer 338, and poloxamer 407.

Of these, homopolymers or copolymers of N-vinyl pyrrolidone, such as copolymers of N-vinyl pyrrolidone and vinyl acetate, are preferred. A non-limiting example of a preferred polymer is a copolymer of 60% by weight of N-vinyl pyrrolidone and 40% by weight of vinyl acetate. Other preferred polymers include, without limitation, hydroxypropyl methylcellulose (HPMC, also known as hypromellose in USP), such as hydroxypropyl methylcellulose grade E5 (HPMC-E5); and hydroxypropyl methylcellulose acetate succinate (HPMC-AS).

A pharmaceutically acceptable surfactant employed in a process of the invention is preferably a non-ionic surfactant. More preferably, the non-ionic surfactant has an HLB value of from 2-20. The HLB system (Fiedler, H. B., Encylopedia of Excipients, 5$^{th}$ ed., Aulendorf: ECV-Editio-Cantor-Verlag (2002)) attributes numeric values to surfactants, with lipophilic substances receiving lower HLB values and hydrophilic substances receiving higher HLB values.

Non-limiting examples of pharmaceutically acceptable surfactants that are suitable for use in a process of the invention include polyoxyethylene castor oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40, also known as polyoxyl 40 hydrogenated castor oil or macrogolglycerol hydroxystearate) or polyethylenglycol 60 hydrogenated castor oil (Cremophor® RH 60); or a mono fatty acid ester of polyoxyethylene sorbitan, such as a mono fatty acid ester of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), or polyoxyethylene (20) sorbitan monolaurate (Tween® 20). Other non-limiting examples of suitable surfactants include polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (Lauroglycol®); sucrose fatty acid esters, e.g. sucrose monostearate, sucrose distearate, sucrose monolaurate, sucrose dilaurate; sorbitan fatty acid mono esters such as sorbitan mono laurate (Span® 20), sorbitan monooleate, sorbitan monopalnitate (Span® 40), or sorbitan stearate. Other suitable surfactants include, but are not limited to, block copolymers of ethylene oxide and propylene oxide, also known as polyoxyethylene polyoxypropylene block copolymers or polyoxyethylene polypropyleneglycol, such as Poloxamer® 124, Poloxamer® 188, Poloxamer® 237, Poloxamer® 388, or Poloxamer® 407 (BASF Wyandotte Corp.).

Non-limiting examples of preferred surfactants for use in a process of the invention include polysorbate 20, polysorbate 40, polysorbate 60, polysorbate 80, Cremophor RH 40, Cremophor EL, Gelucire 44/14, Gelucire 50/13, D-alphatocopheryl polyethylene glycol 1000 succinate (vitamin E TPGS), propylene glycol laurate, sodium lauryl sulfate, and sorbitan monolaurate.

A pharmaceutically acceptable surfactant as used herein can be a mixture of pharmaceutically acceptable surfactants, such as a combination of a surfactant having an HLB value of below 10 and another surfactant having an HLB value of no lees than 10.

In one embodiment, a surfactant having an HLB value of at least 10 is used in a process of the invention. In another embodiment, a surfactant having an HLB value of below 10 is used in a process of the invention. In yet another embodiment, a mixture of two or more surfactants (e.g., a combination of one surfactant having an HLB value of at least 10 and another surfactant having an HLB value of below 10) is used in a process of the invention.

In one embodiment, a process of the invention comprises dissolving a crystalline form of the invention, a hydrophilic polymer described above, and a surfactant described above to form a solution (e.g., a melt). The hydrophilic polymer can be selected, for example, from the group consisting of homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, and polysaccharide. As a non-limiting example, the hydrophilic polymer is selected from the group consisting of homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propiovate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, and xanthan gum. Preferably, the hydrophilic polymer is selected from polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, poloxamer 124, poloxamer 188, poloxamer 237, poloxamer 338, or poloxamer 407. More preferably, the hydrophilic polymer is selected from homopolymers of vinylpyrrolidone (e.g., PVP with Fikentscher K values of from 12 to 100, or PVP with Fikentscher K values of from 17 to 30), or copolymers of 30 to 70% by weight of N-vinylpyrrolidone (VP) and 70 to 30% by weight of vinyl acetate (VA) (e.g., a copolymer of 60% by weight VP and 40% by weight VA). The surfactant can be selected, for example, from the group consisting of polyoxyethyleneglycerol triricinoleate or polyoxyl 35 castor oil (Cremophor® EL; BASF Corp.) or polyoxyethyleneglycerol oxystearate, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, and sorbitan fatty acid mono ester. As a non-limited example, the surfactant is selected from the group consisting of polyethylenglycol 40 hydrogenated castor oil (Cremophor® RH 40, also known as polyoxyl 40 hydrogenated castor oil or macrogolglycerol hydroxystearate), polyethylenglycol 60 hydrogenated castor oil (Cremophor® RH 60), a mono fatty acid ester of polyoxyethylene (20) sorbitan (e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), or polyoxyethylene (20) sorbitan monolaurate (Tween® 20)), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate, sucrose monostearate, sucrose distearate, sucrose monolaurate, sucrose dilaurate, sorbitan monolaurate, sorbitan monooleate, sorbitan monopalnitate, and sorbitan stearate. Preferably, the surfactant is selected from polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, or sorbitan monolaurate. More preferably, the surfactant is selected from sorbitan monolaurate or D-alpha-tocopheryl polyethylene glycol 1000 succinate.

In another embodiment, a process of the invention comprises dissolving a crystalline form of the invention, a hydrophilic polymer described above, and a surfactant described above to form a solution (e.g., a melt). The hydrophilic polymer is a homopolymer or copolymer of N-vinyl pyrrolidone (e.g., copovidone). The pharmaceutically acceptable surfactant can be, e.g., vitamin E TPGS, or sorbitan monolaurate.

A melt-extrusion process of the invention typically comprises preparing a melt from (1) a crystalline form of the invention, (2) a hydrophilic polymer described above (or another suitable binder), and (3) preferably a surfactant described above. The melt can then be cooled until it solidifies. The crystalline form of Compound I initially used will disappear upon the formation of the melt. The melt may also include other additives. "Melting" means a transition into a liquid or rubbery state in which it is possible for one component to get embedded, preferably homogeneously embedded, in the other component or components. In many cases, the polymer component will melt and the other components including the crystalline form of Compound I and the surfactant will dissolve in the melt thereby forming a solution. Melting usually involves heating above the softening point of the polymer. The preparation of the melt can take place in a variety of ways. The mixing of the components can take place before, during or after the formation of the melt. For example, the components can be mixed first and then melted or be simultaneously mixed and melted. The melt can also be homogenized in order to disperse Compound I efficiently. In addition, it may be convenient first to melt the polymer and then to mix in and homogenize Compound I. In one example, all materials except the surfactant are blended and fed into an extruder, while the surfactant is molten externally and pumped in during extrusion.

In another example, the melt comprises Compound I and a hydrophilic polymer described above, and the melt temperature is in the range of from 100 to 170° C., preferably from 120 to 150° C., and highly preferably from 135 to 140° C. The melt can also include a pharmaceutically acceptable surfactant described above.

In still another example, the melt comprises Compound I, at least another anti-HCV agent (e.g., a HCV polymerase inhibitor, or a NS5A inhibitor, or a combination of a HCV polymerase inhibitor and a NS5A inhibitor), and a hydrophilic polymer described above. The melt can also include a pharmaceutically acceptable surfactant described above.

To start a melt-extrusion process, Compound I is employed in a crystalline form of the invention, e.g., any crystalline form described in any aspect, embodiment or example of this application. A crystalline form of the invention may also be first dissolved in a suitable liquid solvent such as alcohols, aliphatic hydrocarbons, esters or, in some cases, liquid carbon dioxide; the solvent can be removed, e.g., evaporated, upon preparation of the melt.

Various additives can also be included in the melt, for example, flow regulators (e.g., colloidal silica), lubricants, fillers, disintegrants, plasticizers, colorants, or stabilizers (e.g., antioxidants, light stabilizers, radical scavengers, and stabilizers against microbial attack).

The melting and/or mixing can take place in an apparatus customary for this purpose. Particularly suitable ones are extruders or kneaders. Suitable extruders include single screw extruders, intermeshing screw extruders or multi-screw extruders, preferably twin screw extruders, which can be corotating or counterrotating and, optionally, be equipped with kneading disks. It will be appreciated that the working temperatures will be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt can range from thin to pasty to viscous. Shaping of the extrudate can be conveniently carried out by a calender with two counter-rotating rollers with mutually matching depressions on their surface. The extrudate can be cooled and allow to solidify. The extrudate can also be cut into pieces, either before (hot-cut) or after solidification (cold-cut).

The solidified extrusion product can be further milled, ground or otherwise reduced to granules. The solidified extrudate, as well as each granule produced, comprises a solid dispersion, preferably a solid solution, of Compound I in a matrix comprised of the hydrophilic polymer and optionally the pharmaceutically acceptable surfactant. Where the granules do not contain any surfactant, a pharmaceutically acceptable surfactant described above can be added to and blended with the granules. The extrusion product can also be blended with other active ingredient(s) (e.g., ritonavir) and/or additive(s) before being milled or ground to granules. The granules can be further processed into suitable solid oral dosage forms.

In one example, copovidone and a surfactant described above are mixed and granulated, followed by the addition of aerosil and a crystalline form of Compound I of the invention. The mixture can also contain ritonavir. The mixture, which may contain for example 5% by weight of Compound I, is then milled. The mixture is then subject to extrusion, and the extrudate thus produced can be milled and sieved for further processing to make capsules or tablets. The surfactant employed in this example can also be added through liquid dosing during extrusion.

The approach of solvent evaporation, e.g., via spray-drying, provides the advantage of allowing for processability at lower temperatures, if needed, and allows for other modifications to the process in order to further improve powder properties. The spray-dried powder can then be formulated further, if needed, and final drug product is flexible with regards to whether capsule, tablet or any other solid dosage form is desired.

Exemplary spray-drying processes and spray-drying equipment are described in K. Masters, Spray Drying Handbook (Halstead Press, New York, 4th ed., 1985). Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus. This help to ensure that the dried droplets are essentially solid and can form a fine powder and do not stick to the apparatus wall. The spray-dried product can be collected by removing the material manually, pneumatically, mechanically or by other suitable means. The actual length of time to achieve the preferred level of dryness depends on the size of the droplets, the formulation, and spray dryer operation. Following the solidification, the solid powder may stay in the spray drying chamber for additional time (e.g., 5-60 seconds) to further evaporate solvent from the solid powder. The final solvent content in the solid dispersion as it exits the dryer is preferably at a sufficiently low level so as to improve the stability of the final product. For instance, the residual solvent content of the spray-dried powder can be less than 2% by weight. Highly preferably, the residual solvent content is within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other processes.

Like the solid extrudate described above, the spray dried product contains a solid dispersion, preferably a solid solution, of Compound I in a matrix comprised of a hydrophilic polymer described above and optionally a pharmaceutically acceptable surfactant described above. Where the spray dried product does not contain any surfactant, a pharmaceutically acceptable surfactant described above can be added to and blended with the spray-dried product before further processing.

Before feeding into a spray dryer, a crystalline form of Compound I of the invention, a hydrophilic polymer described above, as well as other optional active ingredients or excipients such as a pharmaceutically acceptable surfactant described above, can be dissolved in a solvent. Suitable solvents include, but are not limited to, alkanols (e.g., methanol, ethanol, 1-propanol, 2-propanol or mixtures thereof), acetone, acetone/water, alkanol/water mixtures (e.g., ethanol/water mixtures), or combinations thereof. The solution can also be preheated before being fed into the spray dryer. In many cases, ritonavir is dissolved together with the crystalline form of Compound I.

The solid dispersion produced by melt-extrusion, spray-drying or other techniques can be prepared into any suitable solid oral dosage forms. In one embodiment, the solid dispersion prepared by melt-extrusion, spray-drying or other techniques (e.g., the extrudate or the spray-dried powder) can be compressed into tablets. The solid dispersion can be either directly compressed, or milled or ground to granules or powders before compression. Compression can be done in a tablet press, such as in a steel die between two moving punches. When a solid composition comprises Compound I and another anti-HCV agent, it is possible to separately prepare solid dispersions of each individual active ingredient and then blend the optionally milled or ground solid dispersions before compacting. Compound I and another antiHCV agent can also be prepared in the same solid dispersion, optionally milled and/or blended with other additives, and then compressed into tablets. Likewise, when a solid composition comprises Compound I and ritonavir, it is possible to separately prepare solid dispersions of each individual active ingredient and then blend the optionally milled or ground solid dispersions before compacting. Compound I and ritonavir can also be prepared in the same solid dispersion, optionally milled and/or blended with other additives, and then compressed into tablets.

At least one additive, such as one selected from flow regulators, lubricants, fillers, disintegrants or plasticizers, may be used in compressing the solid dispersion. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like.

Various other additives may also be used in preparing a solid composition prepared according to a process of the invention, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack.

In one embodiment, a process of the invention described above (including any process described in any aspect, embodiment, example or preference) uses a crystalline form of Compound I which has characteristic peaks in the powder X-ray diffraction (PXRD) pattern as shown in FIG. 1 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 1 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 3.78, 4.09, 8.19, 9.15, 10.42, 13.02, 13.50, 18.45, 19.48, and 20.86, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 3.78, 4.09, 6.92, 8.19, 9.15, 10.12, 10.42, 12.30, 13.02, 13.50, 14.77, 16.20, 16.97, 18.12, 18.45, 19.48, 20.86, 24.24, 24.79, and 25.97, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 3.78, 4.09, 6.72, 6.92, 8.19, 9.15, 9.84, 10.12, 10.42, 10.72, 11.66, 12.30, 13.02, 13.50, 14.77, 15.26, 15.62, 16.20, 16.97, 17.27, 17.55, 18.12, 18.45, 19.48, 19.90, 20.37, 20.61, 20.86, 21.99, 22.25, 22.72, 24.24, 24.79, 25.97, 26.88, 27.42, 27.81, and 30.23, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 2 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 2 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.70, 7.53, 10.51, 11.43, 11.80, 15.85, 17.23, 19.11, 21.37, and 23.00, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.23, 5.70, 7.53, 8.24, 8.97, 10.51, 11.43, 11.80, 12.05, 12.69, 13.23, 14.97, 15.85, 17.23, 19.11, 20.20, 21.37, 21.99, 22.22, and 23.00, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.23, 5.70, 7.53, 8.24, 8.97, 10.51, 11.43, 11.80, 12.05, 12.69, 13.23, 13.99, 14.97, 15.85, 17.23, 18.45, 19.11, 19.76, 20.20, 21.37, 21.99, 22.22, 23.00, 25.17, 25.43, 26.73, and 32.46, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 3 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 3 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (°2θ) of 5.22, 5.69, 7.55, 10.49, 11.38, 11.84, 15.99, 17.23, 19.18, and 21.41, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (°2θ) of 5.22, 5.69, 7.55, 8.21, 9.40, 10.49, 11.38, 11.84, 12.04, 12.67, 13.24, 15.99, 17.23, 19.18, 20.15, 21.41, 22.10, 22.53, 23.02, and 25.19, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.22, 5.69, 7.55, 8.21, 8.99, 9.40, 10.49, 11.07, 11.38, 11.84, 12.04, 12.67, 13.24, 13.99, 14.96, 15.99, 17.23, 18.10, 18.47, 19.18, 20.15, 21.41, 22.10, 22.53, 23.02, 25.19, 25.69, 26.57, 26.98, 30.09, and 32.45, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 4 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 4 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.43, 6.24, 7.53, 10.91, 12.34, 12.57, 13.67, 13.94, 17.44, and 19.30, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.43, 6.24, 7.53, 8.68, 10.58, 10.91, 12.34, 12.57, 13.67, 13.94, 14.71, 15.40, 15.99, 16.64, 17.44, 19.30, 19.70, 21.10, 21.33, and 21.72, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.43, 6.24, 7.53, 8.68, 9.28, 10.58, 10.91, 11.65, 12.34, 12.57, 13.67, 13.94, 14.71, 15.40, 15.99, 16.64, 17.44, 19.30, 19.70, 21.10, 21.33, 21.72, and 22.78, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 5 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 5 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.57, 6.19, 7.50, 10.86, 11.46, 12.42, 13.59, 15.28, 16.66, and 19.44, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.57, 6.19, 7.50, 8.75, 10.86, 11.08, 11.46, 12.42, 13.59, 15.28, 16.26, 16.66, 17.25, 17.87, 19.44, 20.80, 21.13, 21.39, 22.15, and 27.12, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.57, 6.19, 7.50, 8.75, 10.86, 11.08, 11.46, 12.42, 12.84, 13.59, 15.28, 16.26, 16.66, 17.25, 17.87, 19.44, 20.80, 21.13, 21.39, 22.15, 23.17, 24.15, and 27.12, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 6 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 6 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 4.35, 4.68, 7.33, 12.01, 13.13, 13.35, 16.54, 17.96, 18.26, and 21.21, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 4.35, 4.68, 6.41, 7.33, 9.54, 10.26, 11.13, 11.34, 12.01, 13.13, 13.35, 14.33, 16.54, 17.96, 18.26, 18.60, 19.77, 21.21, 21.75, and 24.19, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 4.35, 4.68, 6.41, 6.92, 7.33, 9.25, 9.54, 10.26, 11.13, 11.34, 12.01, 13.13, 13.35, 14.33, 14.65, 15.36, 16.54, 17.96, 18.26, 18.60, 19.05, 19.77, 21.21, 21.75, and 24.19, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 7 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 7 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.36, 8.81, 10.09, 10.69, 11.43, 12.95, 14.14, 17.96, 18.28, and 22.88, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 3.50, 5.36, 8.81, 10.09, 10.69, 11.43, 12.19, 12.95, 14.14, 14.72, 15.18, 17.53, 17.96, 18.28, 18.86, 21.36, 22.01, 22.88, 26.54, and 28.04, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 3.50, 4.61, 5.36, 5.79, 7.61, 8.81, 10.09, 10.69, 11.43, 12.19, 12.95, 14.14, 14.72, 15.18, 15.64, 16.87, 17.53, 17.96, 18.28, 18.86, 19.76, 21.36, 22.01, 22.88, 24.42, 25.20, 26.54, 28.04, and 28.65, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 8 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 8 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.08, 10.81, 12.05, 13.47, 13.68, 17.68, 19.02, 19.48, 21.73, and 25.53, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.08, 7.82, 10.27, 10.81, 12.05, 13.47, 13.68, 14.95, 16.81, 17.68, 19.02, 19.48, 20.36, 21.73, 22.24, 23.48, 25.53, 26.93, 32.01, and 33.12, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.08, 7.82, 10.27, 10.81, 11.11, 12.05, 13.47, 13.68, 14.95, 15.57, 16.28, 16.81, 17.68, 19.02, 19.48, 20.36, 21.73, 22.24, 23.48, 24.16, 25.53, 26.93, 28.26, 30.41, 31.07, 32.01, 33.12, and 35.04, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 9 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 9 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.31, 11.11, 12.60, 13.75, 15.29, 15.96, 17.62, 19.71, 21.30, and 22.88, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.31, 10.16, 10.62, 11.11, 12.60, 13.75, 15.29, 15.96, 17.62, 18.19, 19.16, 19.71, 20.58, 21.30, 22.40, 22.88, 23.66, 26.40, 26.74, and 33.46, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.31, 10.16, 10.62, 11.11, 12.60, 13.75, 15.29, 15.96, 17.62, 18.19, 19.16, 19.71, 20.58, 21.30, 22.40, 22.88, 23.66, 26.40, 26.74, 28.12, 31.62, and 33.46, and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern as shown in FIG. 10 and which is substantially pure. For example, the crystalline form used can be at least 90% pure, preferably at least 95% pure, or more preferably at least 97%.

In yet another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) as shown in Table 10 and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 7.42, 10.57, 11.84, 13.74, 15.72, 17.36, 19.38, 21.34, 22.07, and 23.36, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the powder X-ray diffraction (PXRD) pattern at values of two theta (° 2θ) of 5.28, 5.65, 7.42, 9.26, 10.57, 10.90, 11.31, 11.84, 12.15, 12.73, 13.74, 15.72, 17.36, 18.04, 19.38, 21.34, 22.07, 22.90, 23.36, and 26.49, and which is substantially pure. For example, the crystalline form used can be at least 90% pure, preferably at least 95% pure, or more preferably at least 97%.

In another embodiment, a process of the invention described above (including any process described in any aspect, embodiment, example or preference) uses a crystalline form of Compound I which has characteristic peaks in the power X-ray diffraction (PXRD) pattern at values of two theta (° 2θ) of 5.28, 5.65, 7.42, 8.02, 8.94, 9.26, 10.57, 10.90, 11.31, 11.84, 12.15, 12.73, 13.14, 13.74, 14.78, 15.72, 16.32, 16.95, 17.36, 18.04, 18.81, 19.38, 21.34, 22.07, 22.90, 23.36, 24.50, 25.13, 25.59, 26.49, 32.24, and 32.93, and which is substantially pure. For example, the crystalline form used can be at least 90% pure, preferably at least 95% pure, or more preferably at least 97%.

In yet another aspect, the present invention features compositions comprising a crystalline form of Compound I of the invention. Any crystalline form described herein (including any crystalline form described in any aspect, embodiment or example) can be used to make a composition of the invention. Preferably, the crystalline form is substantially pure, such as at least 90% pure, preferably at least 95% pure, or more preferably at least 97% pure. In one embodiment, a composition of the invention comprises at least 5% by weight of a substantially pure crystalline form of the invention. In another embodiment, the composition of the invention comprises at least 10% by weight of a substantially pure crystalline form of the invention. In still another embodiment, a composition of the invention comprises at least 5% by weight of one or more crystalline forms of the invention. In yet another embodiment, a composition of the invention comprises at least 10% by weight of one or more crystalline forms of the invention.

Example 1

Preparation of n-Butylamine-$H_2O$ Solvate (Compound I Pattern A)

Amorphous Compound I was suspended in n-butylamine at ambient temperature. Solids were isolated after crystallization and left at ambient conditions for a short period of time prior to characterization.

The crystal structure has been resolved by Single-Crystal XRD. The asymmetric unit contains 4 molecules of n-butylamine, 2 molecules of water and 2 molecules of Compound I. The experimental powder X-ray diffraction patterns (PXRD) are shown in FIG. 1. Peak listing of the experi mental PXRD pattern with relative intensities is given in Table 1.

Several isostructural crystal forms have been obtained from other solvents (e.g., propylamine/H2O, amylamine, n-hexylamine, sec-butylamine/H2O, isobutylamine/H2O, n-butanol/Heptane, 2-butanol/Heptane, n-pentanol/Heptane, EtOH/Pentane, and n-propanol/Pentane) exhibiting very similar experimental PXRD patterns. These crystal forms are labeled "Pattern A" or "Form I" according to their PXRD patterns.

Compound I was initially found to be very difficult to crystallize during early development. Of all the numerous solvent systems investigated, it was unexpected found that only the n-alkylamines (4-6 carbons) led to significant crystallization.

TABLE 1

PXRD Peak Listing of Compound I Pattern A (n-Butylamine-H2O Solvate)

| Peak Position (° 2θ) | Relative Intensity |
|---|---|
| 3.775 | 64.6 |
| 4.087 | 31 |
| 6.718 | 11.5 |
| 6.921 | 24.2 |

TABLE 1-continued

PXRD Peak Listing of Compound I Pattern A (n-Butylamine-H2O Solvate)

| Peak Position (° 2θ) | Relative Intensity |
|---|---|
| 8.19 | 100 |
| 9.151 | 35.7 |
| 9.836 | 12.3 |
| 10.118 | 22.4 |
| 10.419 | 60.6 |
| 10.724 | 12.4 |
| 11.658 | 12.9 |
| 12.304 | 20.3 |
| 13.019 | 39.7 |
| 13.502 | 37.3 |
| 14.772 | 23.2 |
| 15.255 | 11.7 |
| 15.622 | 7.6 |
| 16.196 | 20.9 |
| 16.974 | 19.1 |
| 17.271 | 12.5 |
| 17.548 | 18.4 |
| 18.122 | 19.7 |
| 18.445 | 50.5 |
| 19.478 | 46.5 |
| 19.896 | 11.4 |
| 20.371 | 11.1 |
| 20.609 | 18.3 |
| 20.861 | 41.4 |
| 21.993 | 18 |
| 22.248 | 9.2 |
| 22.724 | 8.4 |
| 24.242 | 26.5 |
| 24.792 | 26.6 |
| 25.967 | 24.1 |
| 26.884 | 6.3 |
| 27.415 | 6.3 |
| 27.812 | 7 |
| 30.226 | 9.5 |

Example 2

Compound I Pattern B Isolated from MEK/Heptane

Amorphous Compound I was dissolved in methyl ethyl ketone (MEK) at ambient temperature and heptane was added. A seed mixture was prepared from different crystalline solids of Compound I including Form I (n-butylamine-H2O solvate) and other Pattern A forms isolated from alkylamines. Solids were isolated after crystallization and left at ambient conditions for a short period of time prior to characterization.

Powder X-ray diffraction pattern and peak listing with relative intensities are shown in FIG. 2 and Table 2, respectively.

TABLE 2

PXRD Peak Listing of Compound I Pattern B (MEK-Heptane Solvate)

| Peak Position (° 2θ) | Relative Intensity |
|---|---|
| 5.228 | 34.9 |
| 5.7 | 48.7 |
| 7.525 | 62 |
| 8.236 | 32.7 |
| 8.97 | 27.6 |
| 10.514 | 53.8 |
| 11.43 | 51.9 |
| 11.801 | 51.1 |
| 12.053 | 41.1 |
| 12.689 | 33.6 |
| 13.227 | 20.6 |
| 13.988 | 20.5 |

TABLE 2-continued

| PXRD Peak Listing of Compound I Pattern B (MEK-Heptane Solvate) | |
|---|---|
| Peak Position (° 2θ) | Relative Intensity |
| 14.973 | 23.8 |
| 15.847 | 47.1 |
| 17.228 | 64.2 |
| 18.449 | 15.6 |
| 19.114 | 45.4 |
| 19.755 | 13.8 |
| 20.195 | 34.3 |
| 21.367 | 100 |
| 21.988 | 25.8 |
| 22.217 | 28 |
| 23.003 | 43.5 |
| 25.165 | 19.7 |
| 25.432 | 13.5 |
| 26.726 | 20 |
| 32.455 | 11.6 |

Example 3

Compound I Pattern B Isolated from MeOH/Diethyl Ether

Amorphous Compound I was dissolved in methanol at ambient temperature and diethyl ether was added. Pattern B seeds were added to the solution. Solids were isolated after crystallization and left at ambient conditions for a short period of time prior to characterization.

Powder X-ray diffraction pattern and peak listing with relative intensities are shown in FIG. 3 and Table 3, respectively.

TABLE 3

| PXRD Peak Listing of Compound I Pattern B (MeOH-Diethyl Ether Solvate) | |
|---|---|
| Peak Position (° 2θ) | Relative Intensity |
| 5.219 | 55.1 |
| 5.686 | 82.8 |
| 7.545 | 63.4 |
| 8.213 | 51.9 |
| 8.99 | 18.9 |
| 9.399 | 19 |
| 10.491 | 100 |
| 11.068 | 15.6 |
| 11.384 | 77.3 |
| 11.841 | 59.3 |
| 12.044 | 34.4 |
| 12.671 | 35.4 |
| 13.243 | 25.1 |
| 13.987 | 18.3 |
| 14.955 | 16 |
| 15.985 | 67.5 |
| 17.226 | 78.1 |
| 18.098 | 11.1 |
| 18.47 | 17.3 |
| 19.176 | 61.2 |
| 20.147 | 37 |
| 21.409 | 71.1 |
| 22.1 | 24 |
| 22.525 | 19.8 |
| 23.021 | 41.6 |
| 25.188 | 27.8 |
| 25.687 | 10.6 |
| 26.568 | 13.9 |
| 26.978 | 18.1 |
| 30.091 | 12.9 |
| 32.453 | 11.7 |

Several other isostructural Pattern B solvates have also been obtained from >15 solvent systems, which have similar PXRD patterns.

Example 4

Compound 1 Anhydrate (Pattern C)

Compound I Pattern B solvate isolated from methanol and diethyl ether was dried under vacuum at 50° C. for two weeks. Solids were equilibrated a short time prior to characterization. Powder X-ray diffraction pattern and peak listing with relative intensities are shown in FIG. 4 and Table 4, respectively.

TABLE 4

| PXRD Peak Listing of Compound I Anhydrate (Pattern C) | |
|---|---|
| Peak Position (° 2θ) | Relative Intensity |
| 5.433 | 100 |
| 6.239 | 81.8 |
| 7.525 | 52.2 |
| 8.684 | 35.7 |
| 9.283 | 15.3 |
| 10.582 | 27.4 |
| 10.914 | 38.5 |
| 11.648 | 20.1 |
| 12.34 | 47.1 |
| 12.568 | 48.6 |
| 13.674 | 78.4 |
| 13.942 | 43 |
| 14.711 | 20.6 |
| 15.398 | 30.4 |
| 15.993 | 27.5 |
| 16.637 | 36.4 |
| 17.44 | 37.8 |
| 19.304 | 53.3 |
| 19.698 | 28.8 |
| 21.102 | 32.5 |
| 21.332 | 36.7 |
| 21.715 | 33.2 |
| 22.776 | 17.1 |

Example 5

Compound I MTBE Solvate (Pattern C)

Compound I Pattern B MTBE solvate was dried under vacuum at 70° C. for two days. Solids were equilibrated a short time prior to characterization. Powder X-ray diffraction pattern and peak listing with relative intensities are shown in FIG. 5 and Table 5, respectively.

TABLE 5

| PXRD Peak Listing of Compound I MTBE Solvate (Pattern C) | |
|---|---|
| Peak Position (° 2θ) | Relative Intensity |
| 5.571 | 98 |
| 6.19 | 100 |
| 7.498 | 34 |
| 8.746 | 22 |
| 10.861 | 32.1 |
| 11.083 | 22.4 |
| 11.458 | 41.3 |
| 12.419 | 57.2 |
| 12.839 | 11.4 |
| 13.59 | 33.5 |
| 15.275 | 56 |
| 16.261 | 28 |
| 16.655 | 33 |

TABLE 5-continued

| PXRD Peak Listing of Compound I MTBE Solvate (Pattern C) | |
|---|---|
| Peak Position (° 2θ) | Relative Intensity |
| 17.25 | 13.2 |
| 17.867 | 16.9 |
| 19.435 | 76.3 |
| 20.796 | 19.4 |
| 21.134 | 21.7 |
| 21.39 | 23.4 |
| 22.147 | 15.9 |
| 23.165 | 12.1 |
| 24.147 | 10.4 |
| 27.12 | 14.2 |

Example 6

Pattern D

Compound I Pattern B MTBE solvate and Pattern C MTBE solvate were combined and suspended in 20 w % ethanol in $H_2O$ at ambient temperature for approximately three weeks. Solids were analyzed by PXRD while still wet. Powder X-ray diffraction pattern and peak listing with relative intensities are shown in FIG. 6 and Table 6, respectively.

TABLE 6

| PXRD peak Listing of Compound I Pattern D (from EtOH/$H_2O$) | |
|---|---|
| Peak Position (° 2θ) | Relative Intensity |
| 4.347 | 63.4 |
| 4.684 | 85.5 |
| 6.413 | 24.0 |
| 6.917 | 15.3 |
| 7.331 | 43.2 |
| 9.246 | 14.9 |
| 9.539 | 17.1 |
| 10.261 | 18.7 |
| 11.127 | 23.1 |
| 11.337 | 27.3 |
| 12.006 | 60 |
| 13.131 | 79.8 |
| 13.354 | 35.3 |
| 14.325 | 34.3 |
| 14.653 | 16 |
| 15.359 | 13.7 |
| 16.536 | 41.1 |
| 17.961 | 100 |
| 18.26 | 37.3 |
| 18.604 | 22.0 |
| 19.054 | 11.4 |
| 19.774 | 16.4 |
| 21.208 | 49.6 |
| 21.754 | 22.5 |
| 24.19 | 31.3 |

Example 7

Compound I Hydrate (Pattern E)

Compound I Pattern D was air dried for approximately 2 h. Powder X-ray diffraction pattern and peak listing with relative intensities are shown in FIG. 7 and Table 7, respectively.

TABLE 7

| PXRD Peak Listing of Compound I Hydrate (Pattern E) | |
|---|---|
| Peak Position (° 2θ) | Relative Intensity |
| 3.495 | 22.7 |
| 4.611 | 6.6 |
| 5.356 | 75.5 |
| 5.786 | 14.3 |
| 7.609 | 8.6 |
| 8.806 | 42.6 |
| 10.091 | 40.1 |
| 10.691 | 40.2 |
| 11.428 | 54.3 |
| 12.193 | 27.6 |
| 12.945 | 40.8 |
| 14.143 | 52.6 |
| 14.715 | 20.7 |
| 15.179 | 30.8 |
| 15.643 | 8.2 |
| 16.873 | 13.8 |
| 17.525 | 26.1 |
| 17.957 | 100 |
| 18.284 | 41.2 |
| 18.86 | 25.3 |
| 19.757 | 11.5 |
| 21.363 | 19.6 |
| 22.006 | 23.7 |
| 22.883 | 34.6 |
| 24.423 | 13.2 |
| 25.203 | 13.9 |
| 26.542 | 21.5 |
| 28.035 | 15.4 |
| 28.654 | 11.7 |

Example 8

Compound I ACN Solvate (Pattern F or Form II)

Compound I Pattern B MTBE solvate was suspended in acetonitrile at ambient temperature over four days. Solids were analyzed by PXRD while still wet. Powder X-ray diffraction pattern and peak listing with relative intensities are shown in FIG. 8 and Table 8, respectively.

TABLE 8

| PXRD Peak Listing of Compound I ACN solvate (Form II) | |
|---|---|
| Peak Position (° 2θ) | Relative Intensity |
| 5.081 | 100 |
| 7.815 | 5.6 |
| 10.274 | 7.6 |
| 10.812 | 18.3 |
| 11.108 | 4.2 |
| 12.052 | 43.6 |
| 13.473 | 17.7 |
| 13.683 | 13.3 |
| 14.948 | 7.1 |
| 15.57 | 2.9 |
| 16.282 | 3 |
| 16.812 | 8.4 |
| 17.684 | 14.1 |
| 19.017 | 13.9 |
| 19.48 | 17.5 |
| 20.358 | 11.8 |
| 21.733 | 47.8 |
| 22.237 | 12 |
| 23.483 | 11.4 |
| 24.155 | 3.3 |
| 25.529 | 27.4 |
| 26.933 | 8.9 |
| 28.264 | 2.7 |
| 30.406 | 2.8 |
| 31.074 | 1.8 |

TABLE 8-continued

| PXRD Peak Listing of Compound I ACN solvate (Form II) | |
|---|---|
| Peak Position (° 2θ) | Relative Intensity |
| 32.013 | 4.8 |
| 33.119 | 4.6 |
| 35.037 | 2.1 |

Example 9

Compound I ACN Solvate (Pattern F or Form II)

Compound I was dissolved in acetonitrile at 40° C. Di-n-butyl ether was charged to prepare a 60% di-n-butyl ether/acetonitrile composition, and the solution was seeded with Form III. The mixture was charged with di-n-butyl ether to a composition of 83% di-n-butyl ether/acetonitrile and cooled to 25° C. Solids were analyzed by PXRD while still wet.

Example 10

Compound I Anhydrate (Pattern G or Form III)

Compound I ACN solvate (Form II) was air dried at ambient temperature for a few minutes. Powder X-ray diffraction pattern and peak listing with relative intensities are shown in FIG. 9 and Table 9, respectively.

TABLE 9

| PXRD Peak Listing of Compound I Anhydrate (Pattern G or Form III) | |
|---|---|
| Peak Position (° 2θ) | Relative Intensity |
| 5.313 | 100 |
| 10.162 | 6.2 |
| 10.623 | 6.5 |
| 11.108 | 9 |
| 12.603 | 34.4 |
| 13.753 | 13.7 |
| 15.291 | 6.7 |
| 15.961 | 9.5 |
| 17.618 | 15.8 |
| 18.192 | 6.7 |
| 19.16 | 3.2 |
| 19.71 | 9 |
| 20.579 | 5.2 |
| 21.296 | 13.5 |
| 22.395 | 4.1 |
| 22.884 | 7.6 |
| 23.662 | 3.9 |
| 26.402 | 6.7 |
| 26.743 | 5.3 |
| 28.124 | 2.1 |
| 31.621 | 2.2 |
| 33.461 | 3.2 |

Example 11

Compound I di-n-Butyl Ether Solvate (Pattern H)

Compound I Pattern G (Form III) and Pattern C solids in an ~1:1 ratio were suspended in di-n-butyl ether at 25° C. for about 3 months. Solids were analyzed by PXRD after a short equilibration time at ambient temperature. Powder X-ray diffraction pattern and peak listing with relative intensities are shown in FIG. 10 and Table 10, respectively.

TABLE 10

| PXRD Peak Listing of Compound I di-n-Butyl Ether Solvate (Pattern H) | |
|---|---|
| Peak Position (° 2θ) | Relative Intensity |
| 5.28 | 32.5 |
| 5.649 | 28.6 |
| 7.421 | 75.9 |
| 8.017 | 15.9 |
| 8.944 | 15.8 |
| 9.259 | 31.4 |
| 10.574 | 73.4 |
| 10.896 | 31.1 |
| 11.309 | 30.2 |
| 11.837 | 52.3 |
| 12.154 | 42.4 |
| 12.734 | 34.1 |
| 13.144 | 22.9 |
| 13.742 | 47.8 |
| 14.778 | 18.4 |
| 15.721 | 100 |
| 16.32 | 22.1 |
| 16.947 | 19.1 |
| 17.359 | 63.2 |
| 18.044 | 26 |
| 18.806 | 22 |
| 19.382 | 54.8 |
| 21.335 | 84.6 |
| 22.072 | 45.3 |
| 22.9 | 28.8 |
| 23.358 | 49.9 |
| 24.504 | 9.4 |
| 25.126 | 17.3 |
| 25.591 | 19.1 |
| 26.49 | 26.2 |
| 32.237 | 10.7 |
| 32.934 | 8.8 |

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A process for making a pharmaceutical composition comprising Compound I

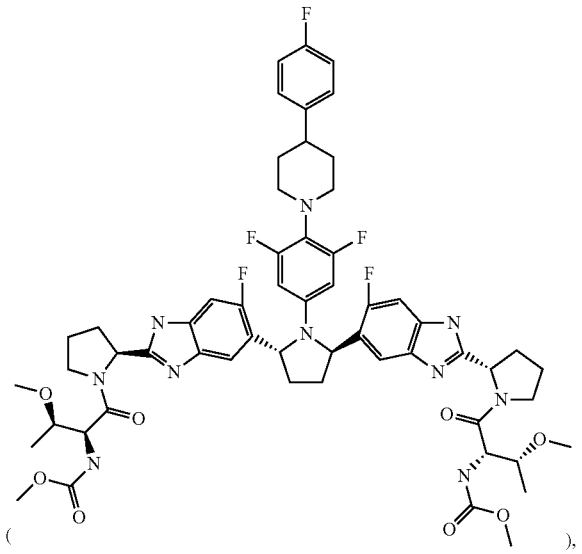

( ), comprising [dissolving] *combining* a crystalline form of Compound I [in a solvent] *with a hydrophilic polymer*, [wherein said crystalline form has characteristic peaks in PXRD pattern as described in one of Tables 1-10 when tested using a diffractometer that is operated with a copper anode tube at 40 kV and 30 mA and a germanium monochromator to provide monochromatic Cu-$K_\alpha$ radiation with a wavelength of 1.54178 Å] *wherein the crystalline form has a powder X-ray diffraction pattern comprising a two theta (° 2θ) peak at about 17.62±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

2. The process of claim 1, wherein [said solvent is a volatile solvent, and said] *the* process further comprises *dissolving Compound I and the polymer in a solvent, and* spray drying the [dissolved Compound I] *resulting solution* to remove the solvent, thereby creating a solid dispersion comprising amorphous Compound I *and the polymer*.

3. The process of claim 1, wherein [said solvent] *the polymer* is a molten or rubbery polymer *in which the crystalline form of Compound I dissolves*, and [said] *the* process further comprises cooling and solidifying the dissolved Compound I, thereby creating a solid dispersion comprising amorphous Compound I and [said polymer] *the polymer*.

[4. The process of claim 1, wherein said characteristic peaks in PXRD pattern are as described in Table 9.]

[5. The process of claim 2, wherein said characteristic peaks in PXRD pattern are as described in Table 9.]

[6. The process of claim 3, wherein said characteristic peaks in PXRD pattern are as described in Table 9.]

[7. A process for making a pharmaceutical composition comprising Compound I, comprising dissolving a crystalline form of Compound I in a solvent, wherein said crystalline form has characteristic peaks in PXRD pattern as described in one of FIGS. 1-10 when tested using a diffractometer that is operated with a copper anode tube at 40 kV and 30 mA and a germanium monochromator to provide monochromatic Cu-$K_\alpha$ radiation with a wavelength of 1.54178 Å.]

[8. The process of claim 7, wherein said solvent is a volatile solvent, and said process further comprises spray drying the dissolved Compound I to remove the solvent, thereby creating a solid dispersion comprising amorphous Compound I.]

[9. The process of claim 7, wherein said solvent is a molten or rubbery polymer, and said process further comprises cooling and solidifying the dissolved Compound I, thereby creating a solid dispersion comprising amorphous Compound I and said polymer.]

[10. The process of claim 7, wherein said characteristic peaks in PXRD pattern are as described in FIG. 9.]

[11. The process of claim 8, wherein said characteristic peaks in PXRD pattern are as described in FIG. 9.]

[12. The process of claim 9, wherein said characteristic peaks in PXRD pattern are as described in FIG. 9.]

[13. A process for making a pharmaceutical composition comprising Compound I,

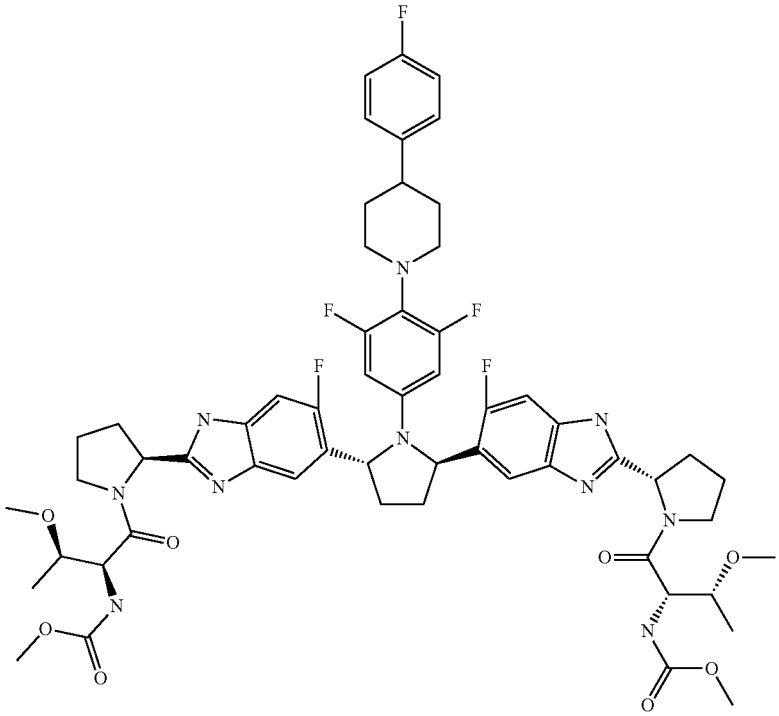

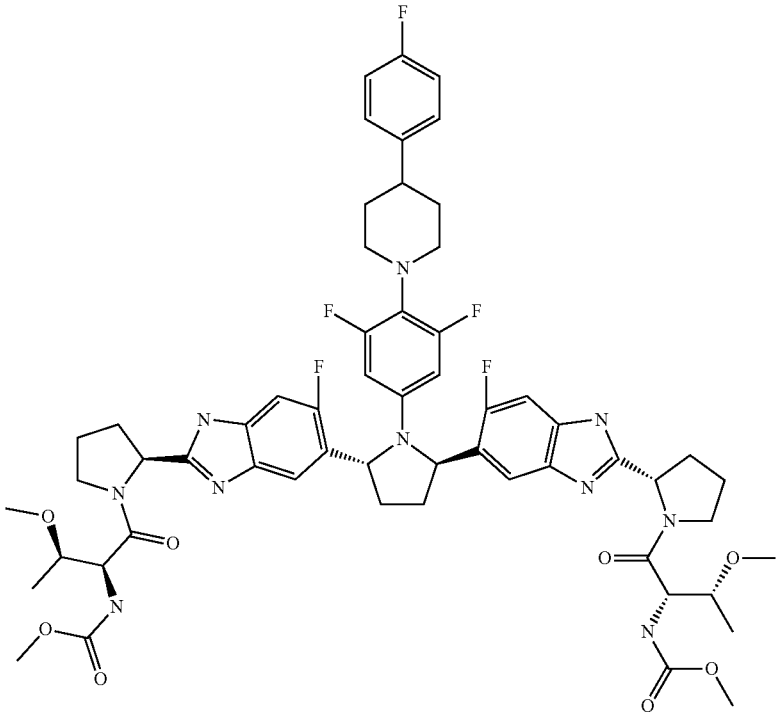

comprising dissolving a crystalline form of Compound I in a solvent, wherein said crystalline form has characteristic peaks in PXRD pattern at values of two theta (° 2θ) of 5.31, 11.11, 12.60, 13.75, 15.29, 15.96, 17.62, 19.71, 21.30, and 22.88 when tested using a diffractometer that is operated with a copper anode tube at 40 kV and 30 mA and a germanium monochromator to provide monochromatic Cu-$K_\alpha$ radiation with a wavelength of 1.54178 Å.]

[14. The process of claim 13, wherein said solvent is a volatile solvent, and said process further comprises spray drying the dissolved Compound I to remove the solvent, thereby creating a solid dispersion comprising amorphous Compound I.]

[15. The process of claim 13, wherein said solvent is a molten or rubbery polymer, and said process further comprises cooling and solidifying the dissolved Compound I, thereby creating a solid dispersion comprising amorphous Compound I and said polymer.]

[16. A process for making a pharmaceutical composition comprising Compound I,

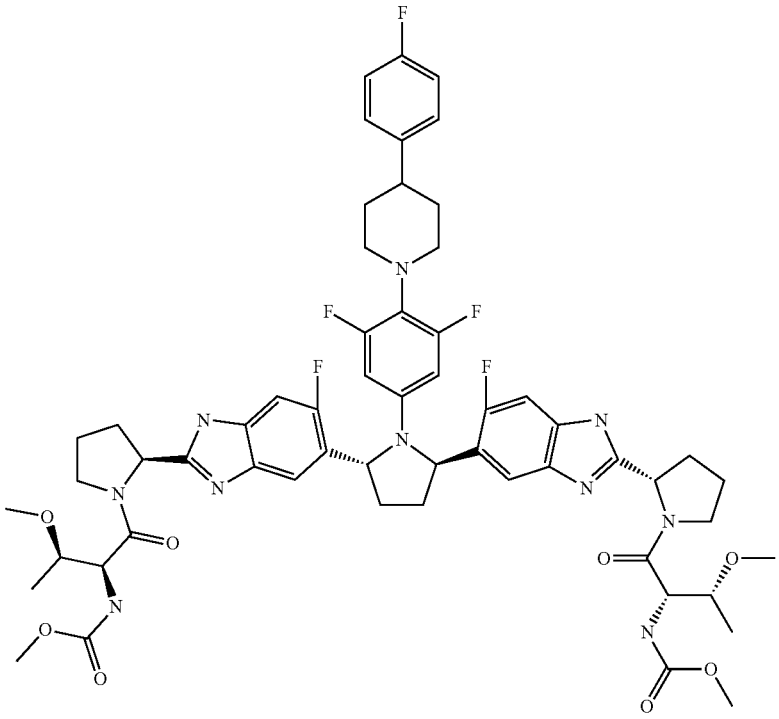

comprising dissolving a crystalline form of Compound I in a solvent, wherein said crystalline form has characteristic peaks in PXRD pattern at values of two theta (° 2θ) of 5.31, 10.16, 10.62, 11.11, 12.60, 13.75, 15.29, 15.96, 17.62, 18.19, 19.16, 19.71, 20.58, 21.30, 22.40, 22.88, 23.66, 26.40, 26.74, and 33.46 when tested using a diffractometer that is operated with a copper anode tube at 40 kV and 30 mA and a germanium monochromator to provide monochromatic Cu-$K_\alpha$ radiation with a wavelength of 1.54178 Å.]

[17. The process of claim 16, wherein said solvent is a volatile solvent, and said process further comprises spray drying the dissolved Compound I to remove the solvent, thereby creating a solid dispersion comprising amorphous Compound I.]

[18. The process of claim 16, wherein said solvent is a molten or rubbery polymer, and said process further comprises cooling and solidifying the dissolved Compound I, thereby creating a solid dispersion comprising amorphous Compound I and said polymer.]

[19. A process for making a pharmaceutical composition comprising Compound I,

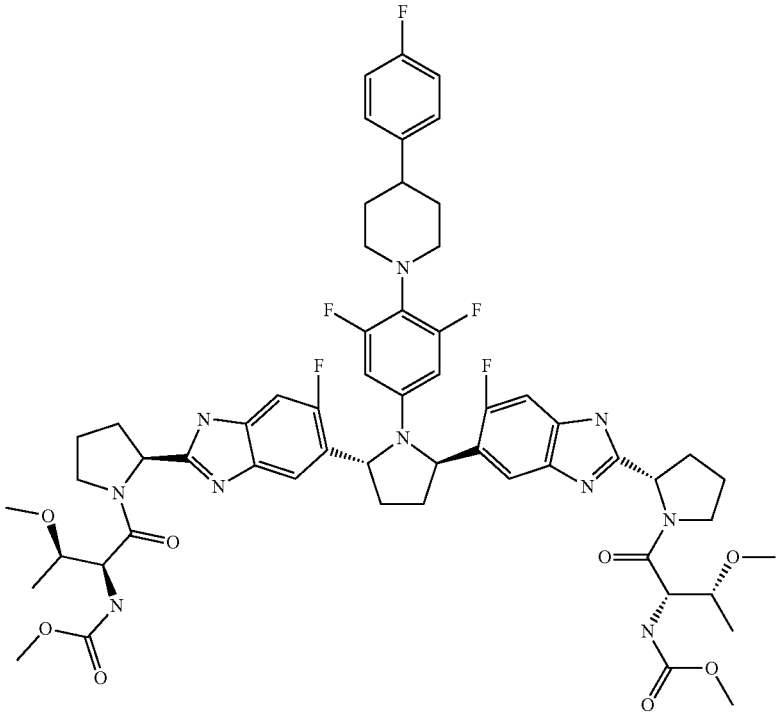

comprising dissolving a crystalline form of Compound I in a solvent, wherein said crystalline form has characteristic peaks in PXRD pattern at values of two theta (° 2θ) of 5.31, 10.16, 10.62, 11.11, 12.60, 13.75, 15.29, 15.96, 17.62, 18.19, 19.16, 19.71, 20.58, 21.30, 22.40, 22.88, 23.66, 26.40, 26.74, 28.12, 31.62, and 33.46 when tested using a diffractometer that is operated with a copper anode tube at 40 kV and 30 mA and a germanium monochromator to provide monochromatic Cu-$K_\alpha$ radiation with a wavelength of 1.54178 Å.]

[20. The process of claim 19, wherein said solvent is a volatile solvent, and said process further comprises spray drying the dissolved Compound I to remove the solvent, thereby creating a solid dispersion comprising amorphous Compound I.]

[21. The process of claim 19, wherein said solvent is a molten or rubbery polymer, and said process further comprises cooling and solidifying the dissolved Compound I, thereby creating a solid dispersion comprising amorphous Compound I and said polymer.]

*22. The process of claim 1, wherein the crystalline form has a powder X-ray diffraction pattern further comprising a two theta (° 2θ) peak at about 13.75±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

*23. The process of claim 22 wherein the crystalline form has a powder X-ray diffraction pattern further comprising a two theta (° 2θ) peak at about 11.11±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

*24. A process for making a pharmaceutical composition comprising Compound I*

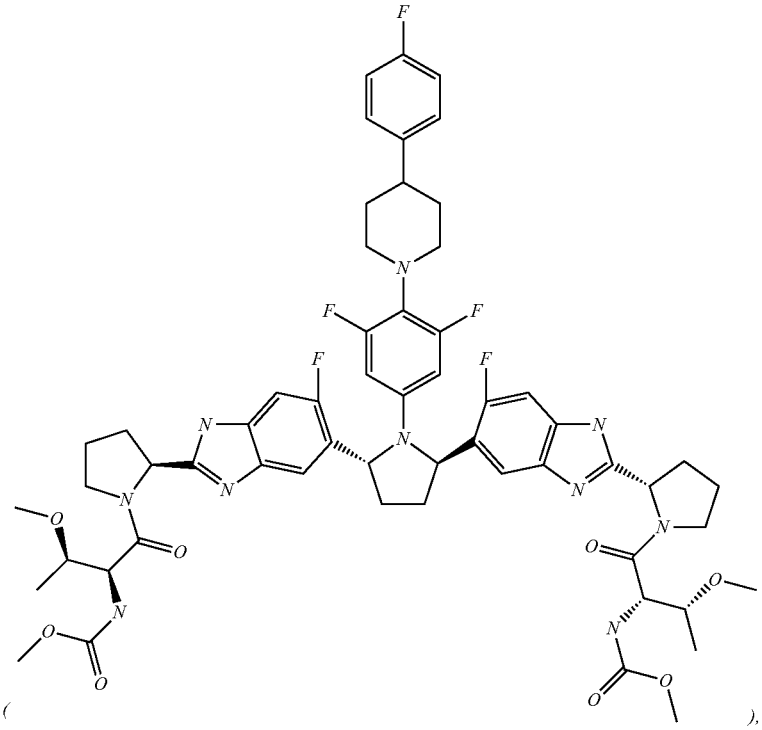

*comprising combining a crystalline form of Compound I with a hydrophilic polymer wherein the crystalline form has a powder X-ray diffraction pattern comprising a two theta (° 2θ) peak at about 10.16±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å, wherein the crystalline form is anhydrous.*

*25. The process of claim 24 wherein the process further comprises dissolving Compound I and the polymer in a solvent, and spray drying the resulting solution to remove the solvent, thereby creating a solid dispersion comprising amorphous Compound I and the polymer.*

*26. The process of claim 24, wherein the polymer is a molten or rubbery polymer in which the crystalline form of Compound I dissolves, and the process further comprises cooling and solidifying the dissolved Compound I, thereby creating a solid dispersion comprising amorphous Compound I and the polymer.*

*27. The process of claim 24, wherein the crystalline form is anhydrous.*

*28. The process of claim 24, wherein the crystalline form has a powder X-ray diffraction pattern further comprising a two theta (° 2θ) peak at about 21.30±0.2° 2θ and about 23.66±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

*29. The process of claim 24, wherein the crystalline form has a powder X-ray diffraction pattern further comprising a two theta (° 2θ) peak at about 5.31±0.2° 2θ, 11.11±0.2° 2θ, 12.60±0.2° 2θ, 13.75±0.2° 2θ, 15.29±0.2° 2θ, 15.96±0.2° 2θ, 19.71±0.2° 2θ, 21.30±0.2° 2θ, and 22.88±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

*30. The process of claim 24, wherein the crystalline form has a powder X-ray diffraction pattern further comprising a two theta (° 2θ) peak at about 5.31±0.2° 2θ, 10.62±0.2° 2θ, 11.11±0.2° 2θ, 12.60±0.2° 2θ, 13.75±0.2° 2θ, 15.29±0.2° 2θ, 15.96±0.2° 2θ, 17.62±0.2° 2θ, 18.19±0.2° 2θ, 19.16±0.2° 2θ, 19.71±0.2° 2θ, 20.58±0.2°2θ, 21.30±0.2° 2θ, 22.40±0.2° 2θ, 22.88±0.2° 2θ, 23.66±0.2° 2θ, 26.40±0.2° 2θ, 26.74±0.2° 2θ and 33.46±0.2° 2θ, when tested using a diffractometer that is operated with a copper anode tube at 40 kV and 30 mA and a germanium monochromator to provide monochromatic Cu-$K_\alpha$ radiation with a wavelength of 1.54178 Å.*

*31. The process of claim 24, wherein the crystalline form has a powder X-ray diffraction pattern of Pattern G.*

*32. A crystalline form of Compound I,*

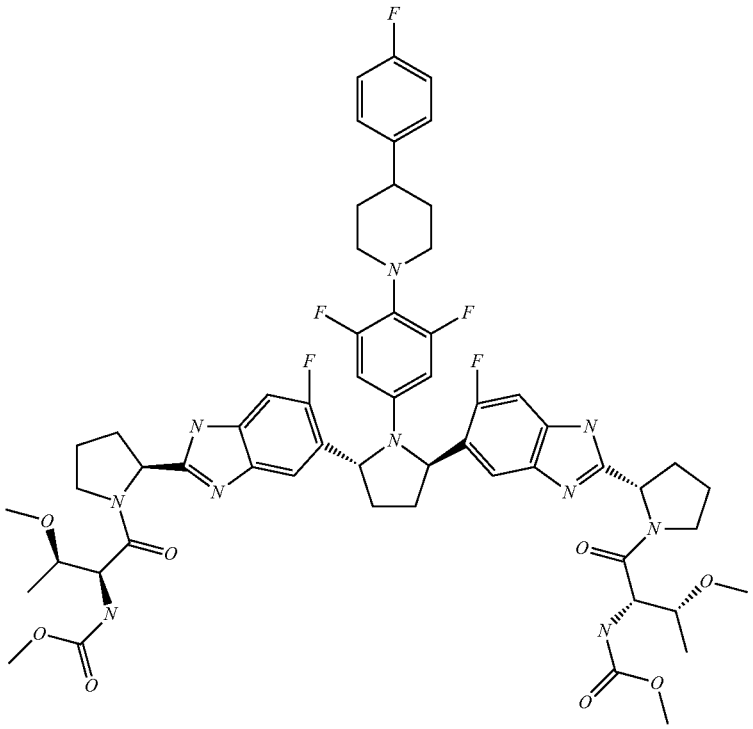

*wherein the crystalline form has a powder X-ray diffraction pattern comprising a two theta (° 2θ) peak at about 17.62±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

*33. The crystalline form of claim 32, wherein the crystalline form has a powder X-ray diffraction pattern further comprising a two theta (° 2θ) peak at about 13.75±0.2° 2θ.*

*34. The crystalline form of claim 33, wherein the crystalline form has a powder X-ray diffraction pattern further comprising a two theta (° 2θ) peak at about 11.11±0.2° 2θ.*

*35. A crystalline form of Compound I,*

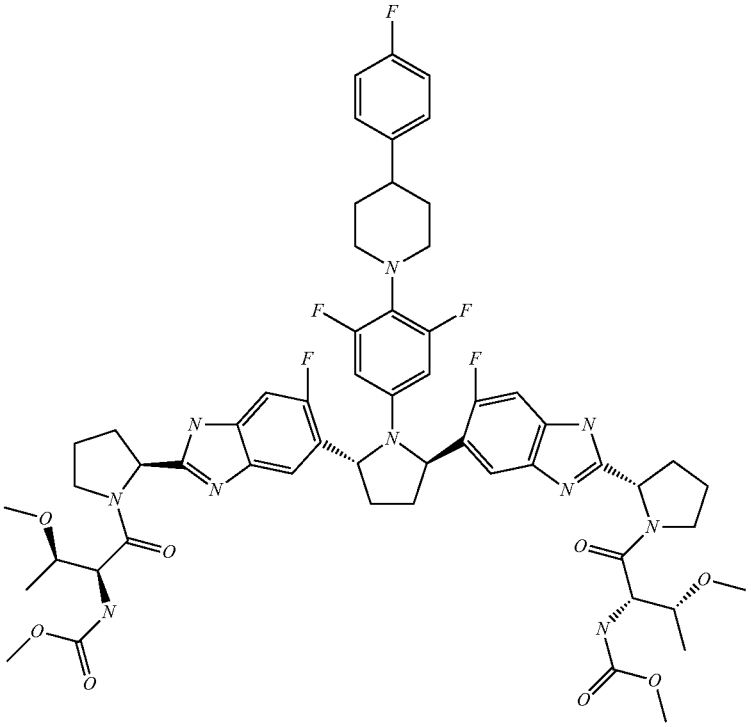

*wherein the crystalline form has a powder X-ray diffraction pattern comprising a two theta (° 2θ) peak at about 10.16±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

*36. The process of claim 35, wherein the crystalline form is anhydrous.*

*37. The crystalline form of claim 35, wherein the crystalline form has a powder X-ray diffraction pattern further comprising a two theta (° 2θ) peak at about 21.30±0.2° 2θ and about 23.66±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

*38. The crystalline form of claim 35, wherein the crystalline form has a powder X-ray diffraction pattern further comprising a two theta (° 2θ) peak at about 5.31±0.2° 2θ, 11.11±0.2° 2θ, 12.60±0.2° 2θ, 13.75±0.2° 2θ, 15.29±0.2° 2θ, 15.96±0.2° 2θ, 19.71±0.2° 2θ, 21.30±0.2° 2θ, and 22.88±0.2° 2θ when tested using a diffractometer that is operated with a copper anode tube at 40 kV and 30 mA and a germanium monochromator to provide monochromatic Cu-$K_\alpha$ radiation with a wavelength of 1.54178 Å.*

*39. The crystalline form of claim 35, wherein the crystalline form has a powder X-ray diffraction pattern further comprising a two theta (° 2θ) peak at about 5.31±0.2° 2θ, 10.62±0.2° 2θ, 11.11±0.2° 2θ, 12.60±0.2° 2θ, 13.75±0.2° 2θ, 15.29±0.2° 2θ, 15.96±0.2° 2θ, 17.62±0.2° 2θ, 18.19±0.2° 2θ, 19.16±0.2° 2θ, 19.71±0.2° 2θ, 20.58±0.2° 2θ, 21.30±0.2° 2θ, 22.40±0.2° 2θ, 22.88±0.2° 2θ, 23.66±0.2° 2θ, 26.40±0.2° 2θ, 26.74±0.2° 2θ and 33.46±0.2° 2θ, when tested using a diffractometer that is operated with a copper anode tube at 40 kV and 30 mA and a germanium monochromator to provide monochromatic Cu-$K_\alpha$ radiation with a wavelength of 1.54178 Å.*

*40. The crystalline form of claim 35, wherein the crystalline form has a powder X-ray diffraction pattern of Pattern G.*

* * * * *